(12) United States Patent
Filipovic et al.

(10) Patent No.: US 11,179,063 B1
(45) Date of Patent: Nov. 23, 2021

(54) INSTANTANEOUS DIRECT COMMUNICATION NETWORK SYSTEM AND METHOD

(71) Applicant: Micro Mobio Corporation, Palo Alto, CA (US)

(72) Inventors: Zlatko Aurelio Filipovic, San Jose, CA (US); Weiping Wang, Palo Alto, CA (US); Adam James Wang, Palo Alto, CA (US); Ikuroh Ichitsubo, Sagamihara (JP); Guan-Wu Wang, Palo Alto, CA (US)

(73) Assignee: Micro Mobio Corporation, Palo Alto, CA (US)

( * ) Notice: Subject to any disclaimer, the term of this patent is extended or adjusted under 35 U.S.C. 154(b) by 0 days.

(21) Appl. No.: 16/586,976

(22) Filed: Sep. 28, 2019

Related U.S. Application Data

(63) Continuation-in-part of application No. 15/614,555, filed on Jun. 5, 2017, now Pat. No. 10,437,295, which
(Continued)

(51) Int. Cl.
*H04W 4/90* (2018.01)
*A61B 5/11* (2006.01)
(Continued)

(52) U.S. Cl.
CPC ............... *A61B 5/1117* (2013.01); *A61B 3/14* (2013.01); *A61B 5/0022* (2013.01); *A61B 5/01* (2013.01); *A61B 5/02438* (2013.01); *A61B 5/1112* (2013.01); *A61B 5/332* (2021.01); *A61B 5/6831* (2013.01); *A61B 5/6898* (2013.01); *A61B 5/742* (2013.01); *A61B 5/748* (2013.01); *G06F 1/163* (2013.01); *G06F 1/1628* (2013.01); *G06F 1/1632* (2013.01); *G06F 1/1633* (2013.01); *G06F 1/1698* (2013.01); *G06F 1/183* (2013.01); *G06F 21/32* (2013.01); *G06F 21/70* (2013.01); *H04B 1/385* (2013.01); *H04B 1/3888* (2013.01); *H04M 1/0254* (2013.01); *H04W 4/90* (2018.02); *A61B 2560/0242* (2013.01); *A61B 2560/0252* (2013.01); *A61B 2560/0257* (2013.01); *A61B 2562/0219* (2013.01); *H04M 1/185* (2013.01); *H04M 1/72409* (2021.01);
(Continued)

(58) Field of Classification Search
CPC ....... A61B 5/1117; A61B 3/14; A61B 5/0022; A61B 5/01
USPC .......................................... 455/557
See application file for complete search history.

(56) References Cited

U.S. PATENT DOCUMENTS

2015/0055622 A1* 2/2015 Roh ................. H04W 28/08 370/331
2016/0360344 A1* 12/2016 Shim ................. H04L 12/2803
(Continued)

*Primary Examiner* — Congvan Tran
(74) *Attorney, Agent, or Firm* — Roark IP

(57) ABSTRACT

The present disclosure relates generally to instantaneous communication network systems and methods and, in particular, in one or more embodiments, the present disclosure relates to a first multi-mode and multi-frequency communication device capable of connecting directly with a proximate second first multi-mode and multi-frequency communication device. A display screen on the communication device is capable of displaying icons and avatars over a map to show other communication devices which are proximate.

24 Claims, 34 Drawing Sheets

Related U.S. Application Data is a continuation-in-part of application No. 14/803,828, filed on Jul. 20, 2015, now Pat. No. 9,671,835, which is a continuation of application No. 13/831,663, filed on Mar. 15, 2013, now Pat. No. 9,086,847.

(60) Provisional application No. 62/738,856, filed on Sep. 28, 2018, provisional application No. 61/705,383, filed on Sep. 25, 2012.

(51) Int. Cl.
| | | |
|---|---|---|
| *A61B 5/00* | (2006.01) | |
| *A61B 5/01* | (2006.01) | |
| *A61B 3/14* | (2006.01) | |
| *G06F 21/70* | (2013.01) | |
| *G06F 21/32* | (2013.01) | |
| *G06F 1/18* | (2006.01) | |
| *H04M 1/02* | (2006.01) | |
| *H04B 1/3888* | (2015.01) | |
| *G06F 1/16* | (2006.01) | |
| *H04B 1/3827* | (2015.01) | |
| *A61B 5/024* | (2006.01) | |
| *A61B 5/332* | (2021.01) | |
| *H04W 88/08* | (2009.01) | |
| *H04W 4/80* | (2018.01) | |
| *H04W 84/12* | (2009.01) | |
| *H04W 84/04* | (2009.01) | |
| *H04M 1/18* | (2006.01) | |
| *H04M 1/72409* | (2021.01) | |
| *H04M 1/72412* | (2021.01) | |

(52) U.S. Cl.
CPC .......... *H04M 1/72412* (2021.01); *H04W 4/80* (2018.02); *H04W 84/04* (2013.01); *H04W 84/12* (2013.01); *H04W 88/08* (2013.01)

(56) References Cited

U.S. PATENT DOCUMENTS

| | | | | |
|---|---|---|---|---|
| 2016/0364811 | A1* | 12/2016 | Chen | G06Q 50/01 |
| 2017/0105131 | A1* | 4/2017 | Song | H04W 4/70 |
| 2017/0357417 | A1* | 12/2017 | Goossens | G06F 3/04845 |
| 2018/0129747 | A1* | 5/2018 | Hale | G06F 16/9535 |
| 2018/0183529 | A1* | 6/2018 | Coutts | G01R 29/10 |
| 2019/0108686 | A1* | 4/2019 | Spivack | G06F 3/0482 |
| 2019/0327363 | A1* | 10/2019 | Raleigh | H04L 12/14 |
| 2019/0342519 | A1* | 11/2019 | Van Os | H04L 51/04 |
| 2019/0392394 | A1* | 12/2019 | Druck | G06F 3/041 |
| 2021/0122391 | A1* | 4/2021 | Hanada | A01B 69/00 |
| 2021/0126703 | A1* | 4/2021 | Macneille | H04B 7/18504 |

* cited by examiner

1419

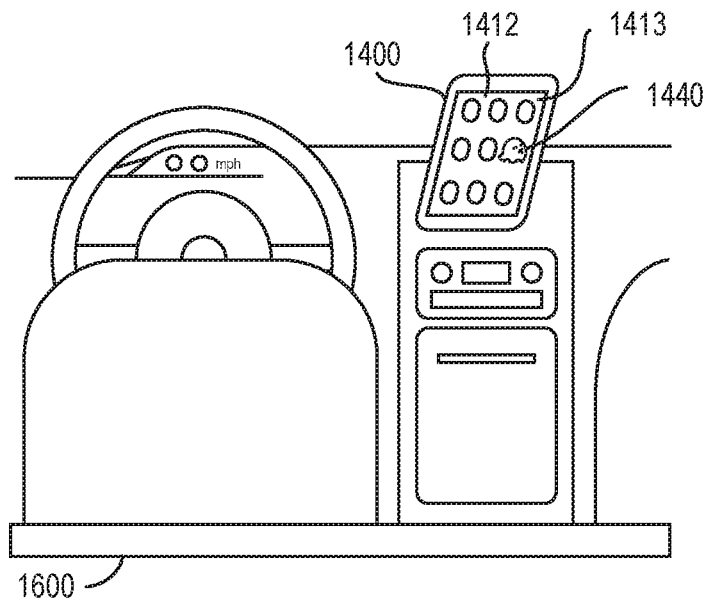
FIG. 25A
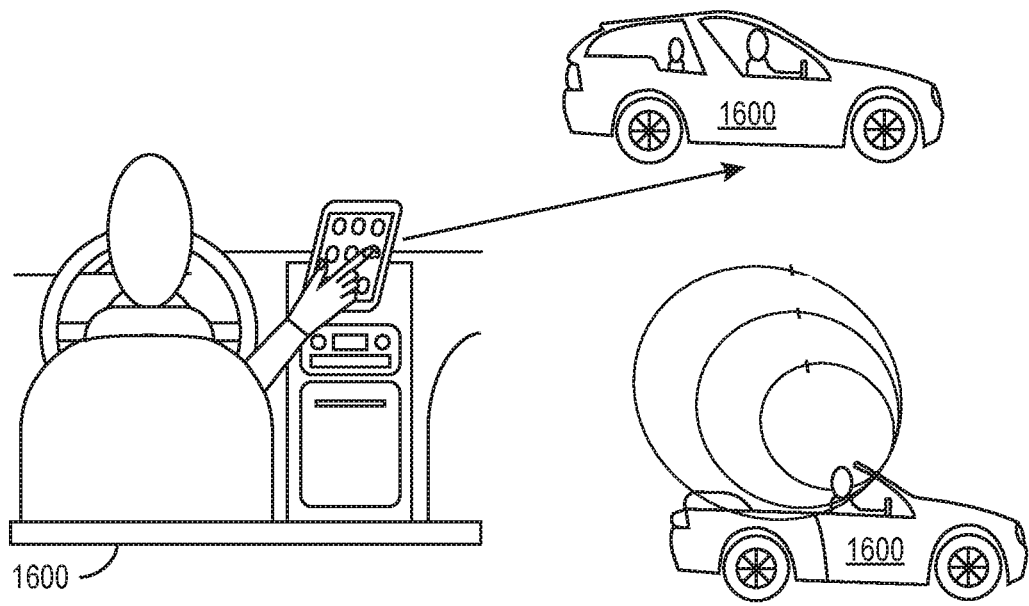
FIG. 25B
FIG. 25C

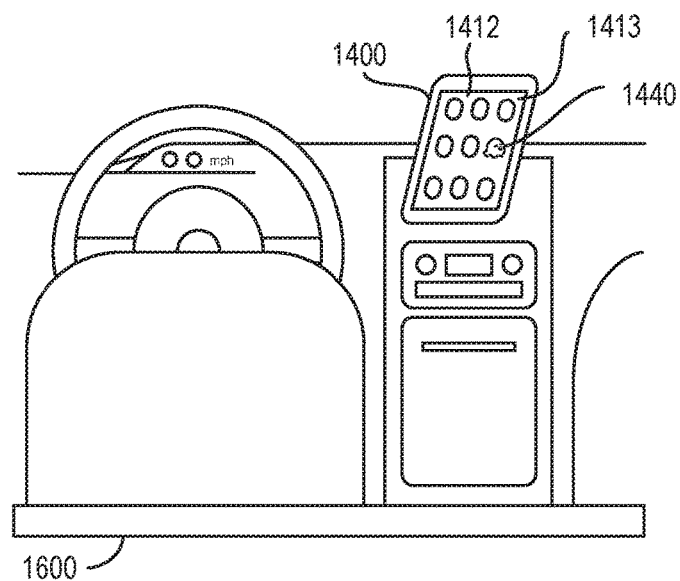
FIG. 26A
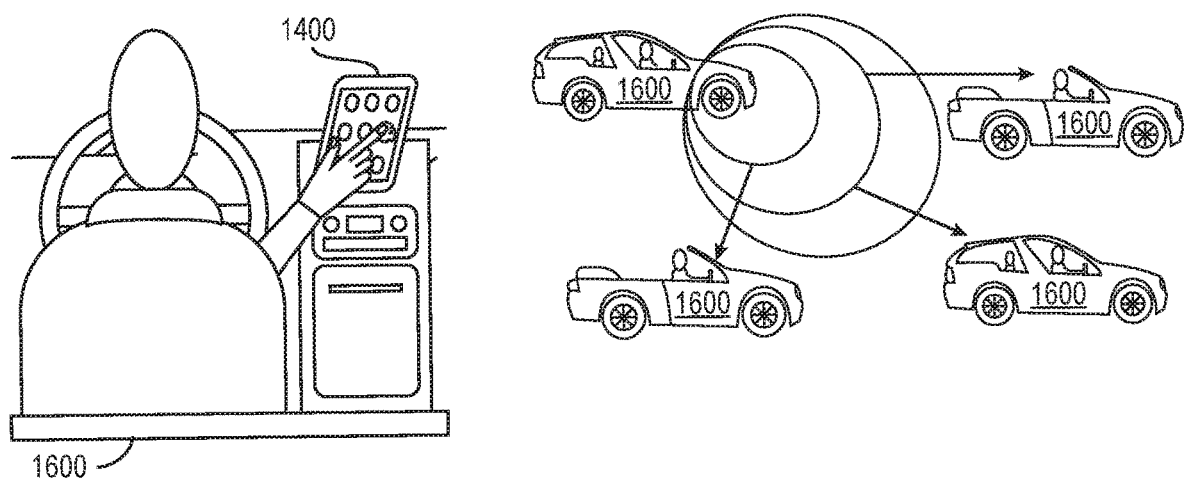
FIG. 26B
FIG. 26C

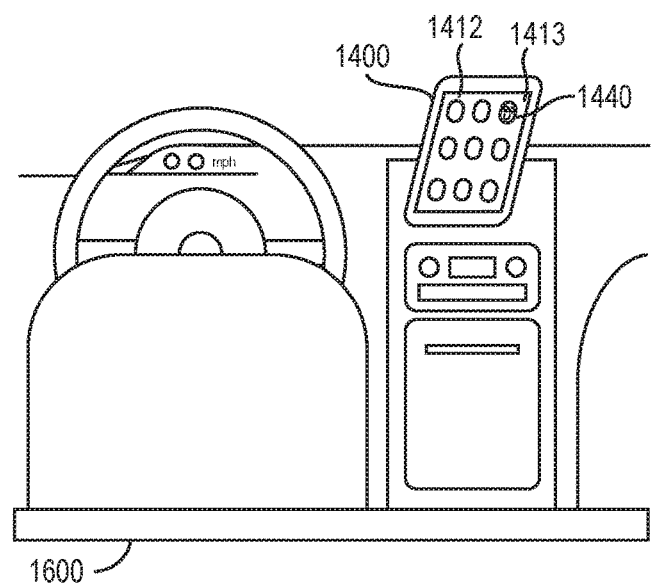
FIG. 27A
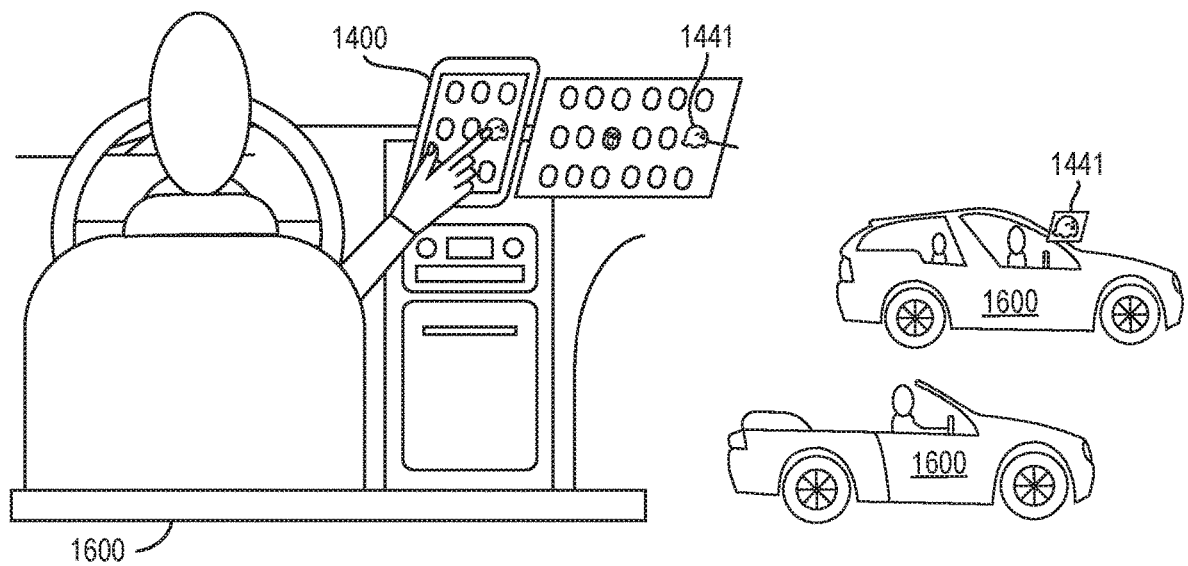
FIG. 27B
FIG. 27C

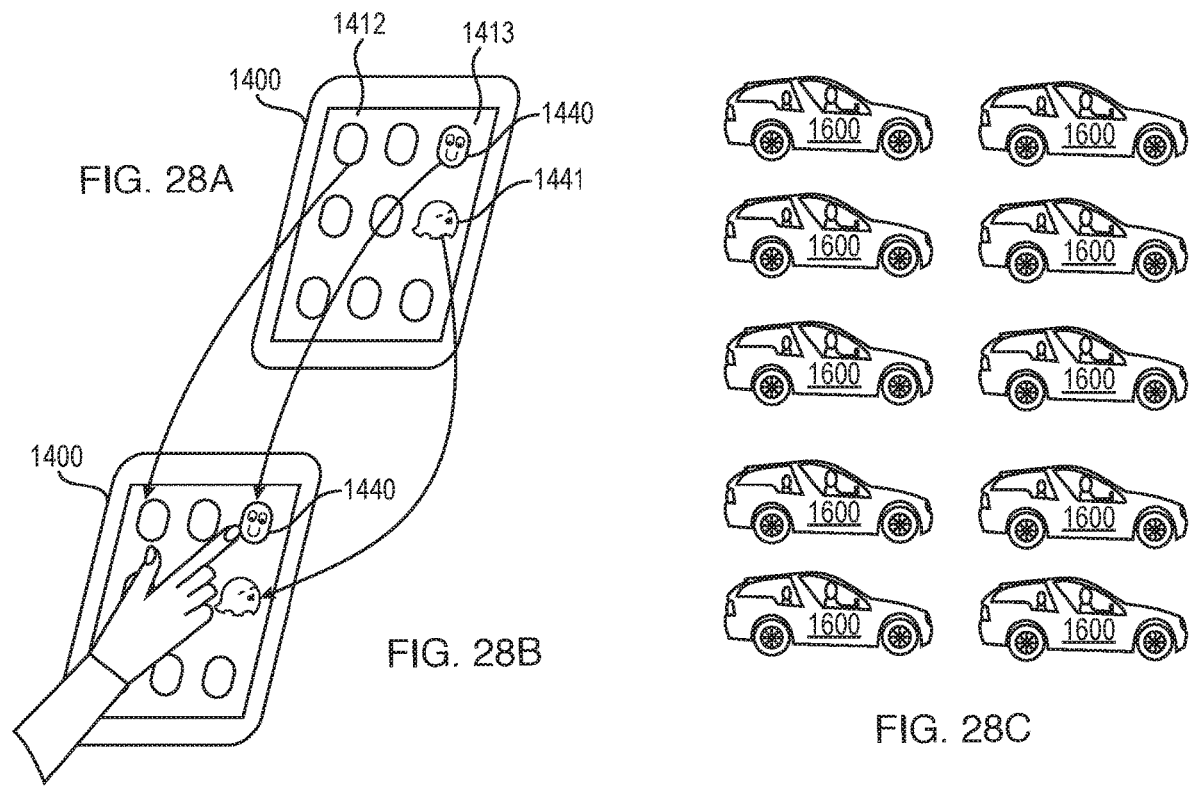
FIG. 28A
FIG. 28B
FIG. 28C
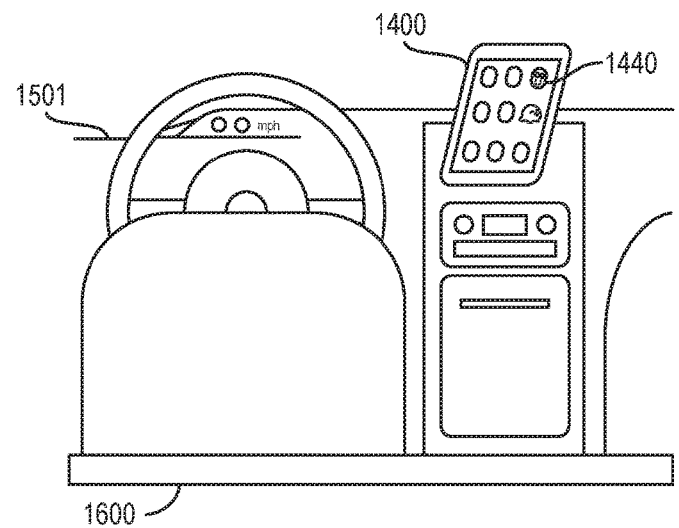
FIG. 29

INSTANTANEOUS DIRECT COMMUNICATION NETWORK SYSTEM AND METHOD

PRIORITY CLAIM

This patent application claims priority as a non-provisional application to U.S. Provisional Patent Application No. 62/738,856, filed on Sep. 28, 2018 and as a Continuation-In-Part of U.S. patent application Ser. No. 15/614,555, filed on Jun. 5, 2017; which claims priority as a Continuation-In-Part of U.S. patent application Ser. No. 14/803,828, filed on Jul. 20, 2015; which claims priority as a Continuation of U.S. patent application Ser. No. 13/831,663, filed on Mar. 15, 2013; which claims the benefit of U.S. Provisional Patent Application Ser. No. 61/705,383, filed Sep. 25, 2012; the aforementioned applications all being incorporated herein by reference in their entirety.

FIELD OF THE DISCLOSURE

The present disclosure relates generally to instantaneous communication network systems and methods and, in particular, to a first multi-mode and multi-frequency communication device capable of connecting directly with a proximate second multi-mode and multi-frequency communication device.

BACKGROUND

Radio frequency (RF) signals typically have a frequency spectrum that can range from several Megahertz (MHZ) to tens of Gigahertz (GHZ) and higher. This allows for the option of wireless communication devices to communicate through a number of different frequencies.

SUMMARY

Aspects of the embodiments disclosed herein include a system comprising: a first wireless communication device having multi-mode and multi-frequency communication capabilities, a microphone and a speaker to enable voice communications, at least one status light emitting diode (LED) to indicate connection status, and wherein the first wireless communication device is capable of receiving a plurality of signals from a plurality of proximity wireless communication devices including a second wireless communication device; and at least one input which is capable of being activated to transmit wireless signals directly to and receive signals directly from the second wireless communication device to form a communication link.

Further aspects of the embodiments disclosed herein include a system comprising: a first wireless communication device having a display screen and multi-mode and multi-frequency capabilities, wherein the first wireless communication device when activated is configured to: send signals directly to and receive signals directly from a plurality of proximate wireless communication devices, wherein said plurality of proximate wireless communication devices appear as a plurality of icons on the display screen; receive a selection of one of the plurality of icons; and form a direct communication link between the first wireless communication device and the selected proximate wireless communication device.

BRIEF DESCRIPTION OF THE DRAWINGS

FIGS. 25A-25C show the steps in setting up a chat.

FIGS. 26A-26C show the steps in setting up a broadcast.

FIGS. 27A-27C show the steps in sending an emoji.

FIGS. 28A-28C show the steps in advertising from a store.

FIG. 29 shows the system application 2504 using a voice.

DETAILED DESCRIPTION

Although particular aspects or features of the following disclosure may be described with reference to one or more particular embodiments and/or drawings, it should be understood that such features are not limited to usage in the one or more particular embodiments or drawings with reference to which they are described, unless expressly specified otherwise. The functionality and/or the features of the embodiments that are described may be alternatively embodied by one or more other devices which are described but are not explicitly described as having such functionality/features.

Current mobile computing device covers are limited in their functionality by mainly providing protection from environmental shocks for mobile computing devices. However, the personal cloud cover case (or "PCCC") as disclosed in this application by providing electronic component accessories and functionalities to the cover case enhances the ability of a mobile computing device located inside the PCCC to provide cloud computing services. Cloud computing is the use of computing resources that are delivered as a service over a network (such as the Internet) and which reside in the "cloud". The mobile computing device in the case could be an iPad®, iPhone®, PC tablet, Android® based tablet, Touch Pad, Nexus 7®, Slate® or the like.

Figure 1B:
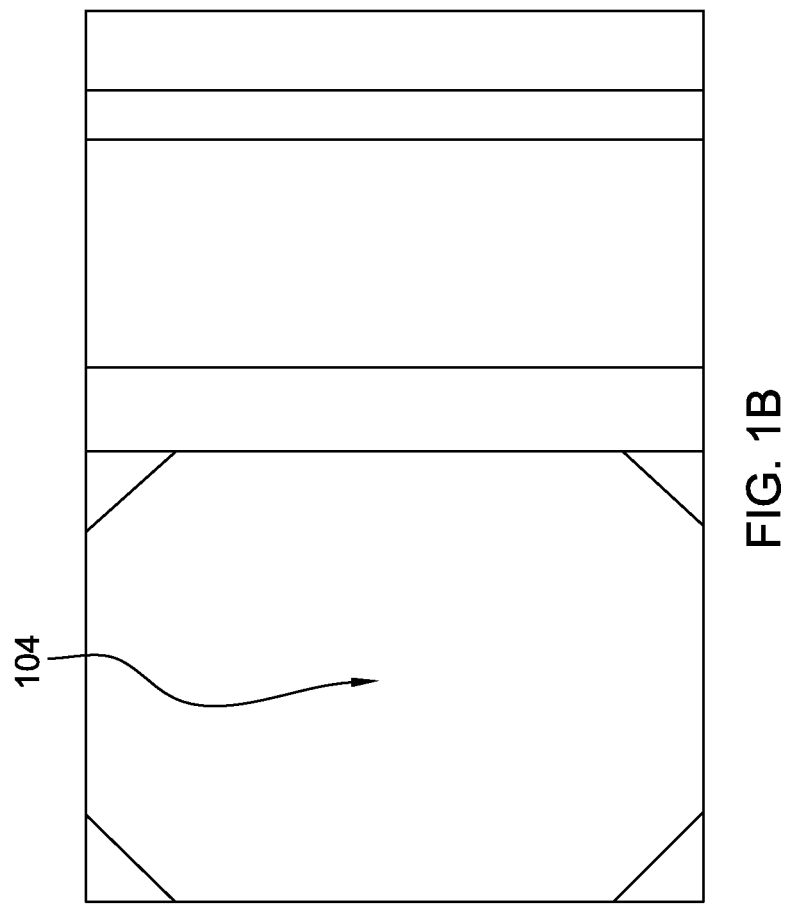
FIG. 1B is a front view of a prior art simple case cover for a mobile computing device.
Figure 1A:
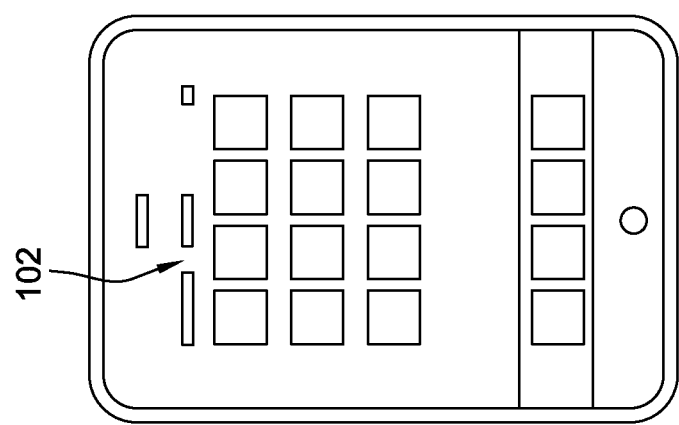
FIG. 1A is a front view of a prior art mobile computing device.
Figure 2A:
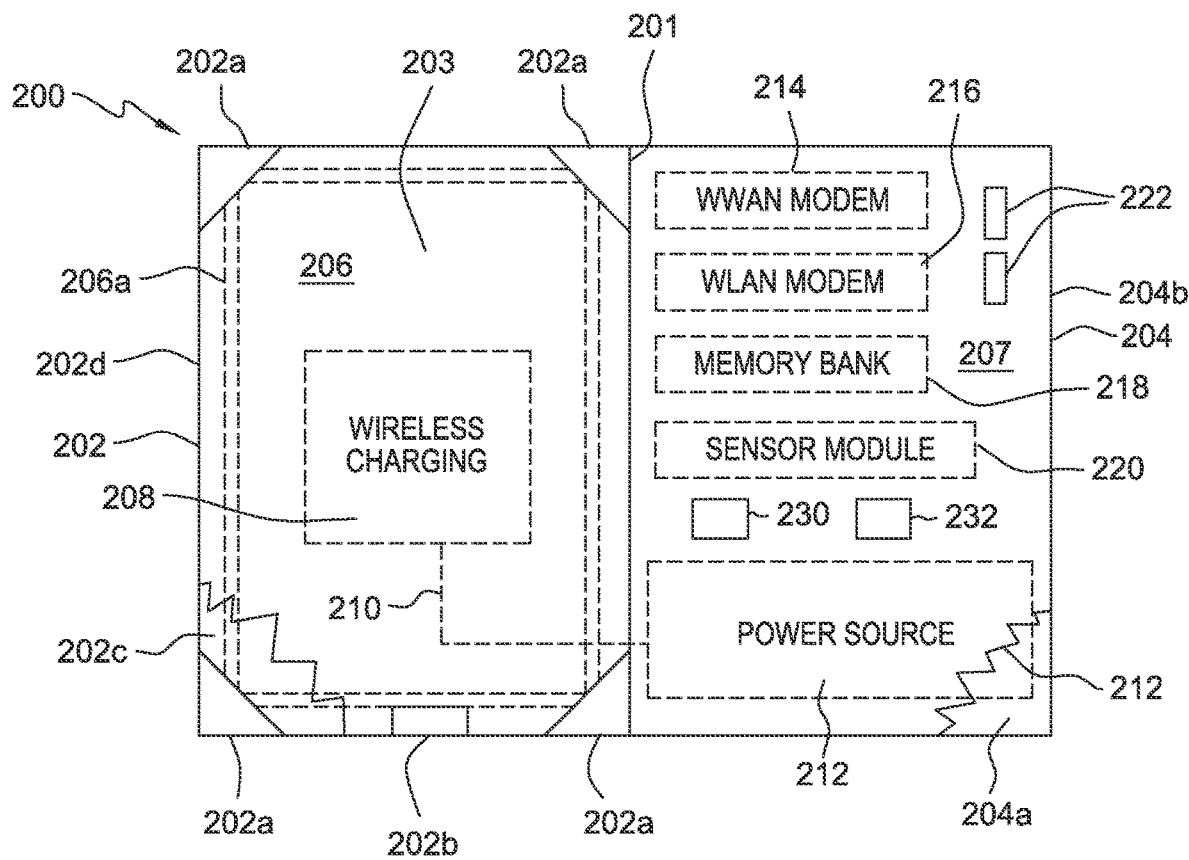
FIG. 2A is a front view of a personal cloud case cover (PCCC).

FIG. 2A is a front view of a PCCC 200 which is shown in an open position. The case 200 provides a personal cloud to the user and access to a wireless network (such as 3G, 4G, 5G, WiFi, SuperWifi, and similar technologies) of a mobile computing device (not shown) stored in the case 200. The case 200 may be made of any material (hard and/or soft) that makes the case lightweight but durable and resilient such as plastic, silicone, ceramic, fabric, leather, steel, aluminum, fiberglass, titanium, Kevlar, or rubber. The case 200 could be a continuous piece of material with a flexible (or bendable) area 201 located between two opposing panels (first panel 202 and second panel 204) which pivot together around a compartment 203 for containing the mobile computing device. In an alternative embodiment, the case 200 could be made up of plurality of attached sections (201, 202 and 204). First panel 202 also has 4 sleeves 202a to hold the mobile computing device in place in the case 200. In alternative embodiments, the mobile computing device could be attached to the PCCC 200 using a plurality of magnets (instead of the sleeves 202a) positioned under the mobile device, rubber straps or other similar attachment methods.

The first panel 202 is constructed in layers and includes inner first panel layer 202c, outer first panel layer 202d and embedded circuit board 206. Typically, from the front view the circuit board 206 cannot be seen since it is located underneath the first panel layer 202c shown in cutaway but which is designed to cover substantially the entire first panel 202. An antenna 206a is located on the circuit board 206 and may be in contact with the mobile communication device wirelessly, through physical contact or by connector 202b. Connector 202b is optional and in alternative embodiments it would not be present. The antenna 206a will allow for better transmission and reception on the part of the mobile communication device. The antenna 206a can be a "chip" antenna, printed circuit board (PCB) antenna or the like covering a plurality of wireless bands (e.g., 400 MHz-3.6 GHz). Alternatively, a PCB antenna may be used, and the antenna 206a will be printed directly onto the circuit board 206. Also located on the board 206 is a two-way wireless charging unit 208 which is in substantial proximity to the resting place of the mobile communication device in the cover 200. The charging unit 208 is designed such that when the mobile communication device is in proximity to the charging unit an electromagnetic field generated by the charging unit pulls the communication device into proper position and alignment for optimal charging (i.e., charging coil alignment). The wireless charging unit 208 is connected through a bidirectional electrical link 210 to power source 212 located on a circuit board 207 embedded in the second panel 204. The bidirectional electrical link 210 is an example of the plurality of electrical connections that are made throughout the case 200 but which are not necessarily shown in the Figures. Link 210 might be in the form of a ribbon cable so as not to be damaged with the opening and closing of the case 200. The wireless charging unit 208 is capable of wirelessly charging the mobile communication device with power received from the power source 212 or wirelessly receive power from the mobile communication device and transfer it to the power source 212. The wireless charging unit 208 may operate by magnetic resonance, inductive charging, or power over radio frequency (RF) or similar wireless charging methods. The power source 212 is used to power the plurality of components located throughout the cover 200 and, as described, can also be used as a backup battery for the mobile computing device when the voltage in the battery of the mobile computing device falls below a predetermined level.

The second panel 204 can be made up of an inner second panel 204a and an outer second panel 204b containing the embedded circuit board 207 but which typically cannot be seen from a front view since it is covered by inner second panel layer 204a. The inner second panel layer 204a covers substantially the entire second panel 204 but is only partially shown in cutaway so as to illustrate the components mounted on the circuit board 207 in the outer second panel 204b. It should be understood that the inner second panel layer 204a and the outer second panel layer 204b can be coupled together by a variety of methods such as ultrasonic bonding, mechanical fasteners, adhesives, or solvents. In alternative embodiments, the inner second panel 204a may be entirely or substantially detachable from the outer second panel 204b; the inner second panel 204a may be a closure flap that is fastened close by means of adhesive, a snap button, or Velcro or the inner second panel 204a may not be present at all so as to allow easy access to the components mounted on the board 207 in the outer second panel 204b. The case 200 may further be made up of a plurality of modules 214, 216, 218 and 220 mounted on the circuit board 207 which allow the PCCC 200 to have multi-functional capability. The modules may be made of low profile components which help minimize the thickness of the cover. The plurality of modules may be permanently mounted, may snap-in to the board 207 or may be some combination thereof. First module 214 may include a wireless wide area network modem (WWAN). The \J\M/AN could include baseband, a radio frequency integrated circuit (RFIC), a radio frequency front-end module (RF FEM), Envelope Tracking (ET), Power Management IC (PMIC), and other connected components to link the mobile computing device to a mobile network such as a 3G, 4G or future generation network. Second module 216 may include a wireless local area network (WLAN) modem for a mobile computing device to connect to a local router and then to 2G, 3G and 4G networks. The WLAN modem can be baseband, RFIC, RF FEM and other connectivity components. The case 200 may contain near field communications (NFC) technology which may be used for contactless short range communications based on RF identification standards (RFID) using magnetic field induction to enable communication between the electronic components in the case 200 over short distances such as a few centimeters. In other embodiments, the WLAN modem connection could be made using wireless protocols such as WiFi, SuperWiFi (i.e., the next generation WiFi with superior range), Bluetooth, wireless for high definition multimedia interface (WHDMI), or the like. Third module 218 may be internal storage such as solid-state drives (SSD) or flash memory (e.g., MultiMedia Card (MMC), electronic MMC (eMMC) or the like). Fourth module 220 may contain a sensor chip that is able to detect biometrics inputs such as finger prints, eye movement, face shape, and the like. Module 220 can be used for functions such as a security feature for allowing or denying access to the electronic components in the case, gaming, and medical purposes (e.g., measuring blood cell count and the like). The second panel 204 may also include a smart feature such as a synchronization input 230 (e.g., such as a button, touch screen, or the like) that allows the plurality of electronic components (e.g., module 218) in the PCCC 200 to be synched to other networked devices in the cloud when operated. This input 230 would primarily be used when a mobile communication device is not present in the PCCC 200. The input 230 may be used to backup data stored in the components of the PCCC 200. Reference 232 in FIG. 2A shows a controller which may be used with the mobile communication device or in the absence of the mobile device to control the electronic components in the PCCC 200. For example, in the synching process when input 230 is operated the controller 232 would direct the synching operation.

Figure 2B:
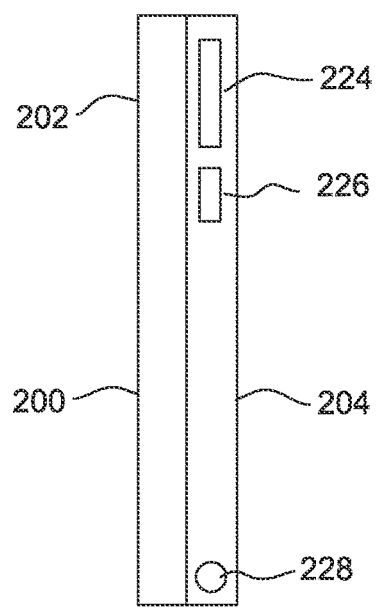
FIG. 2B is a side view of the PCCC of FIG. 2A.

FIG. 2B is a side view of the case 200 in a closed position. Data connection ports 224 and 226 provide communication capabilities to the case 200. Ports 224 and 226 may be a mini universal serial bus (USB), micro universal USB port or an audio visual (AV) connector such as a high definition multimedia interface (HDMI) port and the like. Charging port 228 can be connected to the grid or other power source to feed the power source 212.

Figure 3:
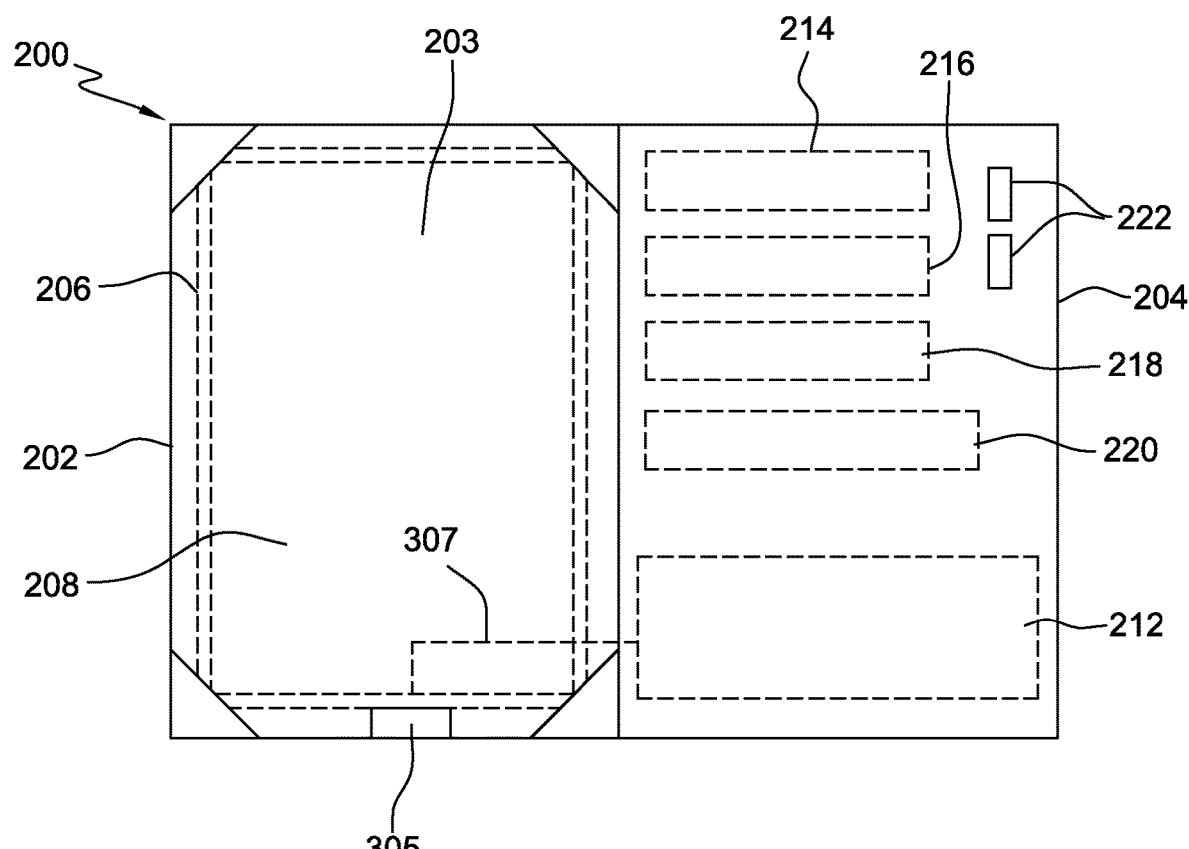
FIG. 3 is a front view of a second embodiment of the PCCC.

FIG. 3 is a second embodiment of the PCCC 200. Common numbering is used in FIGS. 3 though 9 and FIGS. 2A to 2B to denote similar elements. In this second embodiment, instead of wireless charging, a docking bay 305 having a set of electrical contacts is configured to electrically engage with the input/output contacts on a mobile communication device. The docking bay 305 may be a standard connector that allows the mobile communication device to receive power through line 307 from power source 217.

Figure 4:
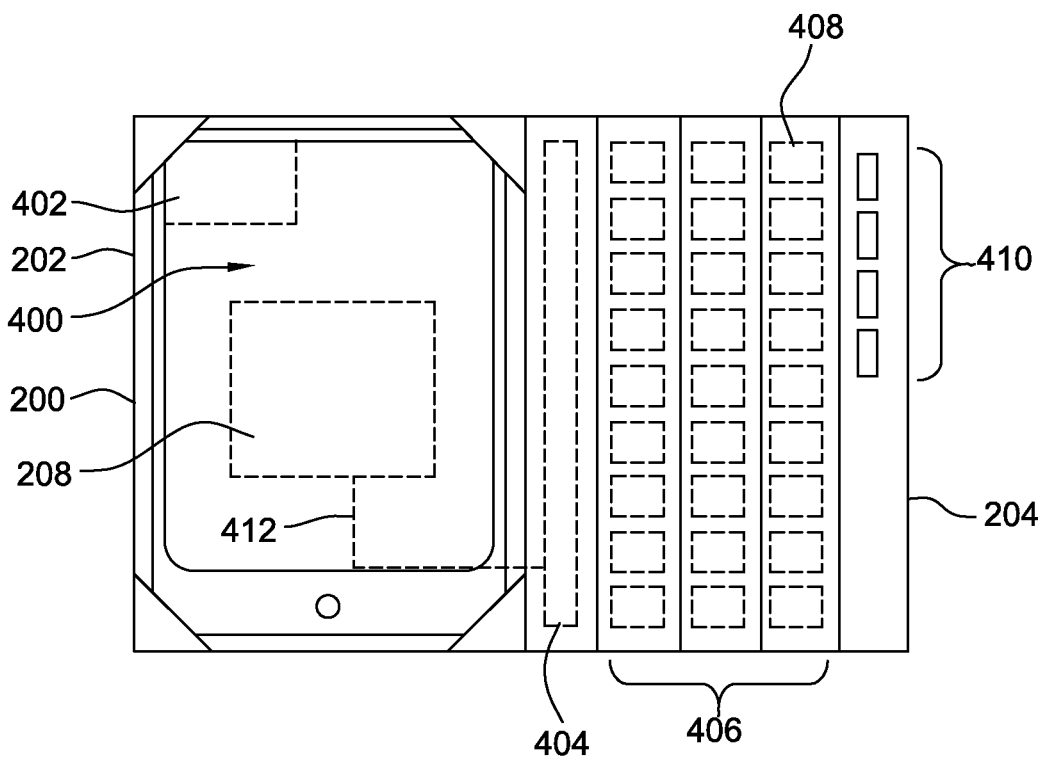
FIG. 4 is a front view of a third embodiment of the PCCC.

FIG. 4 illustrates a third embodiment of the PCCC 200. A mobile communication device 400 can be connected to a local area or wide area network through wireless modem 402 which may be 3G, 4G, 3G/4G, 5G, WHDMI, Bluetooth, WiFi, SuperWiFi, and other wireless standard. Module 404 is a replaceable, rechargeable battery that is charged through line 412 from the wireless charger 208 and receives power from mobile communication device 400. Module 404 performs the same function as power source 212 in FIG. 2 but is arranged differently in the case 200 as shown in FIG. 4. The wireless charger 208 may be located on the first panel 202 beneath the mobile communications device 400. The module 404 can also be charged from a power outlet when the case 200 is plugged in. The module 404 can be used as a power source for other modules (reference numerals 408 and 410 as discussed below) located in the case 200. An embedded memory bank 406 includes a plurality of memory modules and is mounted on the second panel 204. The memory bank modules may be 500 MegaByte (MB), 1 Gigabyte (GB), 1 Terrabyte (TB) or the like in memory size. Memory slots 410 are capable of holding additional memory such as removable micro-Secure Digital (micro-SD) memory cards for storage expansion.

Figure 5:
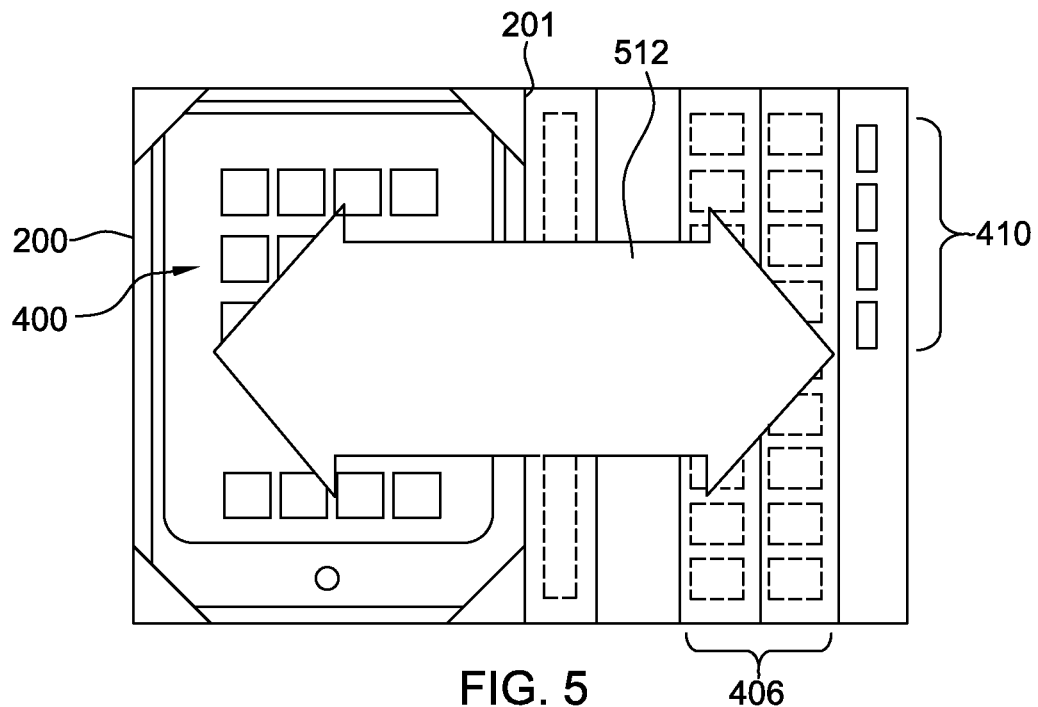
FIG. 5 is a front view of a fourth embodiment of the PCCC.

FIG. 5 illustrates a fourth embodiment of the PCCC 200 which demonstrates that the plurality of modules are detachable and could be two instead of three in the case 200. Also, FIG. 5 discloses a wireless data connection 512 between the device 400 and memory bank 406 using WiFi, SuperWiFi or Bluetooth protocols. In alternate embodiments, the data connection 512 could be a hardwired such as a Universal Serial Bus (USB), microUSB, miniUSB, or HDMI (with the data line being flexibly bendable across the flexible region 201 in the form of a ribbon cable or the like). In other embodiments, the connection could also be an optical wireless link or cable such as infrared. The data transfer could be bi-directional to allow for read and write both ways from device 400 to memory 406 and from memory 406 to device 400.

Figure 6A:
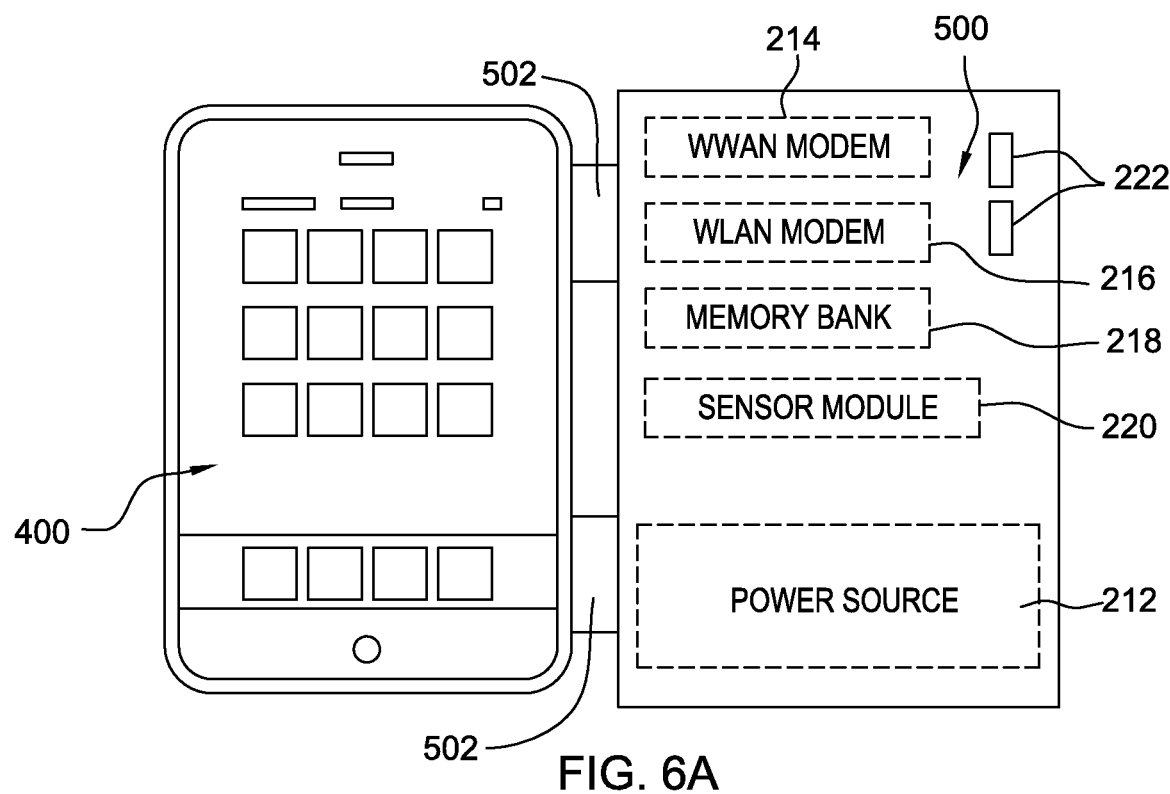
FIG. 6A is a front view of a fifth embodiment of the PCCC.
Figure 6B:
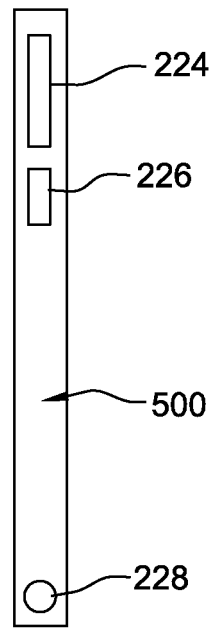
FIG. 6B is a side view of the PCCC of FIG. 6A.

FIG. 6A is another embodiment of the PCCC with just one panel 500 attached to the device 400 through attachments 502. Attachments 502 may be magnets, clip ins, connectors or some other type of hinge. The attachments 502 may internally include a plurality of electrical links to provide power from the power source 212 to the mobile communication device 400 as well as provide data communications between the modules on the panel 500 and the device 400. The power source 212 may include a wireless charging unit so as to wirelessly charge the device 400. The charging may take place when the panel 500 is in a lateral position relative to the device 400 as shown in FIG. 6A. In an alternative embodiment, the panel 500 may be folded over and placed in contact with the device 500 to establish an electrical power link between the power source 212 and electrical contacts located on the device 400. Also, similar to the embodiment of FIG. 5, a wireless data connection may be established between the device 400 and the plurality of modules on the panel 500 (items 214, 216, 218, 220, and 222). FIG. 6B is a side view of the panel 500 showing the connection ports 224, 226, and 228 which serve the same functions as described in connection with FIG. 2B above.

Figure 7:
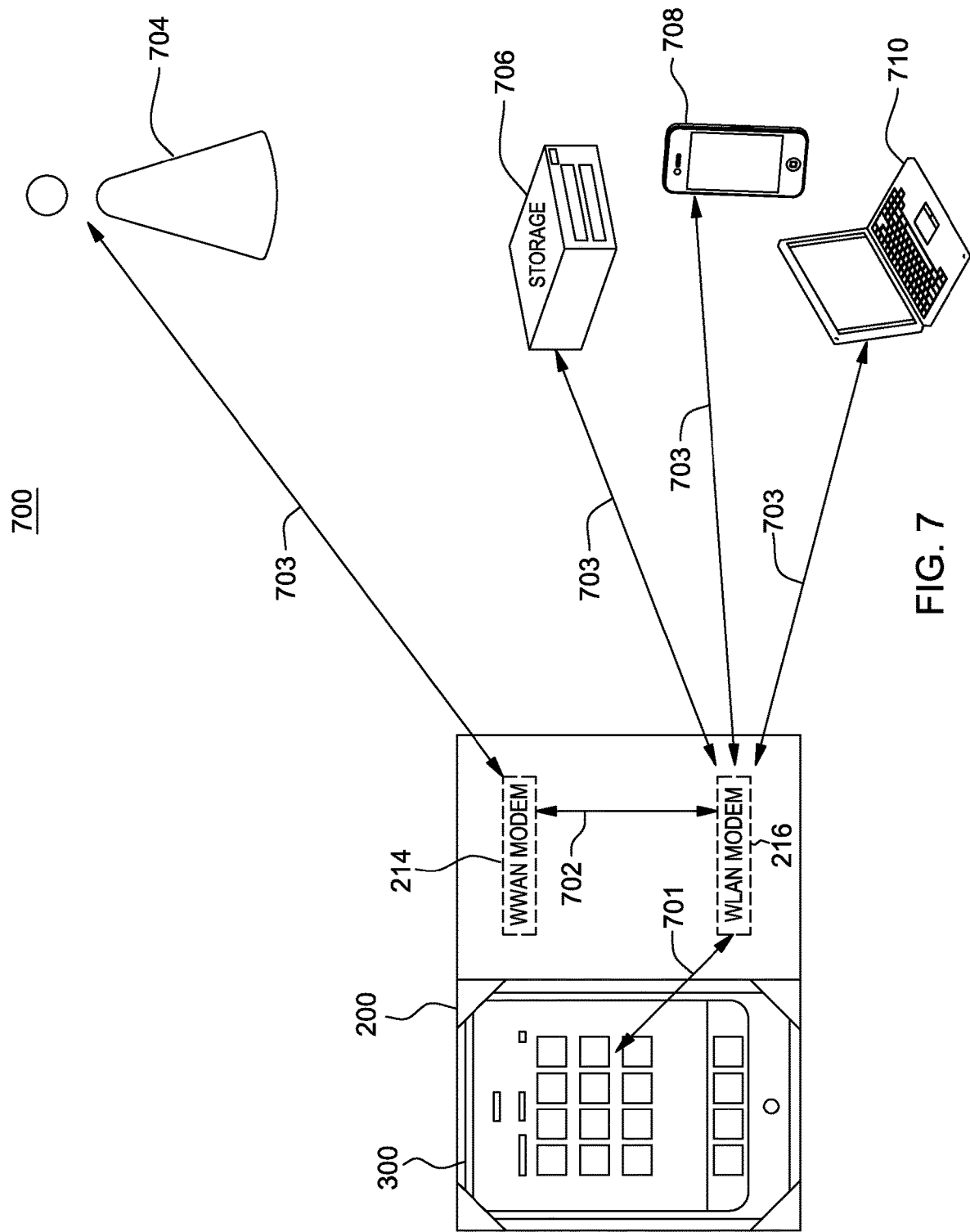
FIG. 7 is a schematic diagram of a PCCC in a cloud/networked environment utilizing 3rd Generation (3G), 4th Generation (4G), Fifth Generation (5G) and similar wireless connections.

FIG. 7 illustrates the mobile communication device 300 and PCCC 200 operating in a cloud (or networked) environment 700. Storage 706, mobile phone 708 and personal computer (PC) 710 are part of the cloud upon which the mobile communications device 300 and PCCC 200 can exchange data and synchronize through a plurality of wireless links 703. The \J\M/AN modem module 214 and the WLAN modem module 216 of FIG. 7 operate in a similar manner as described in connection with FIG. 2A above. The mobile computing device 300 communicates through a bi-directional wireless link 701 with the WLAN modem 216 using Bluetooth, WiFi, SuperWiFi and similar wireless standards. In another embodiment, the link 701 may be a wired link. WLAN modem 216 then can read and write wirelessly in a local environment with storage 706. The WLAN modem 216 can also communicate with another mobile phone 708 and PC 710. Alternatively, the mobile computing device 300 can communicate through WLAN 216 over a bi-directional link 702 with \J\M/AN modem 214. WWAN modem 214 can communicate wirelessly using 3G/4G protocols over longer distances than the WLAN modem 216 with a cell tower 704 and then to the Internet. In the environment of FIG. 7, the case 200 is acting as "hotspot". As a hotspot, the case 200 offers network (e.g., Internet) access over the \J\M/AN modem 214 or WLAN modem 216.

Figure 8:
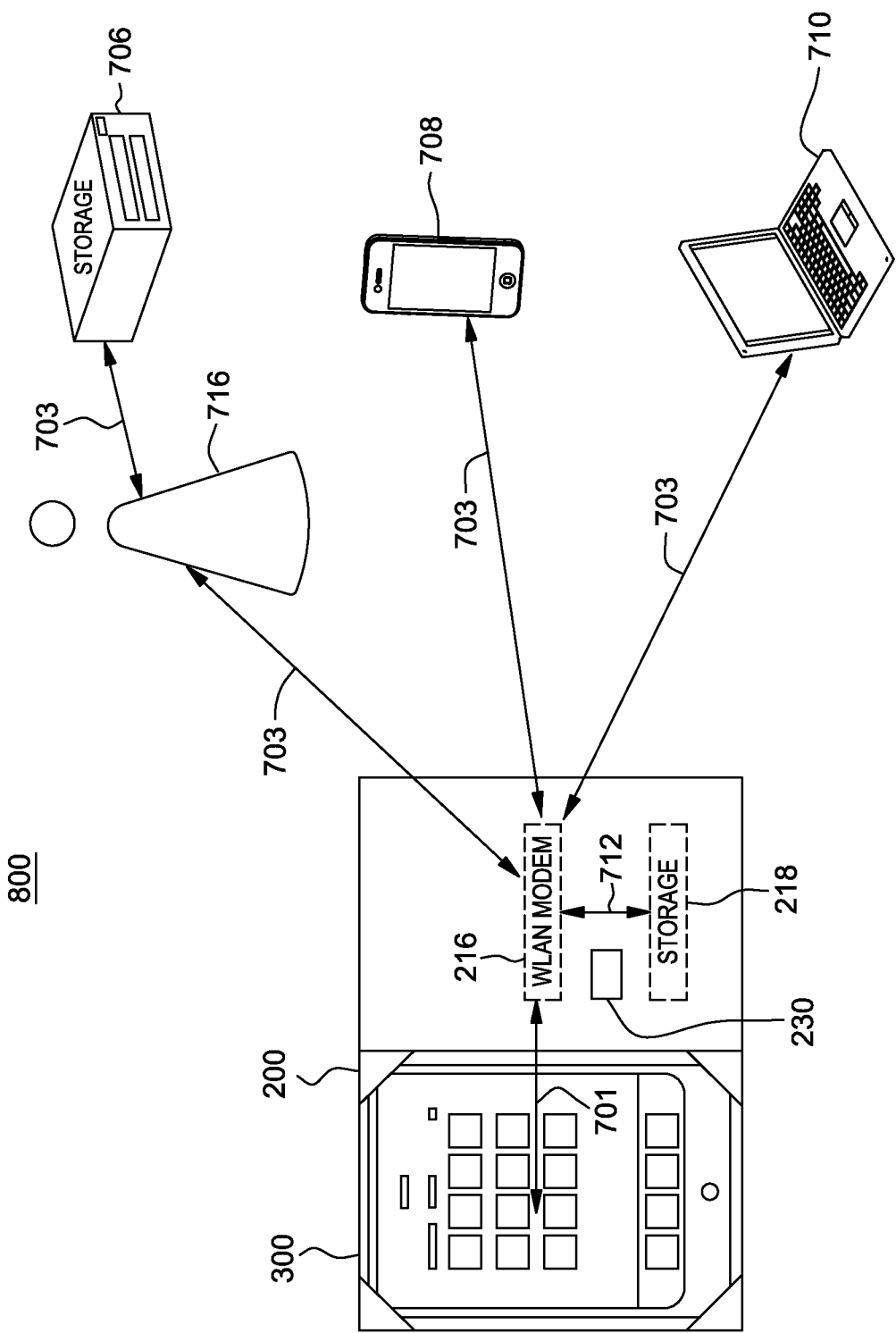
FIG. 8 is a schematic diagram of the PCCC in another cloud/networked environment system.

FIG. 8 illustrates another variation of the mobile communication device 300 and the case 200 in operation 800. This arrangement allows the local storage 218 to have access to a plurality of devices in the cloud such as the communication device 708, PC 710 and storage 706 through local wireless router (or access point) 716. As previously discussed in connection with FIG. 2A, sync input 230 can be operated when the mobile communication device is not present in the case 200 to backup all data contained in the components in the case 200 to the cloud (e.g., devices such as 706, 708, 710 and other devices). Another advantage is that this system allows for the formation of a "pass through Internet" from the mobile communication device 300 to devices 706, 708, 710 and a network (e.g., the Internet). WLAN modem 216 is connected to memory storage 218 through link 712 and is capable of establishing wireless communications with both the mobile communication device 300 and the devices 706, 708, and 710. In operation, the mobile communication device 300 establishes a wireless connection 701 through WiFi, SuperWiFi, 4G or the like to the WLAN modem 216. Through WLAN modem 216, the communication device 300 is capable of connecting to the memory storage 218 (e.g., providing information or instructions regarding reading and/or writing) while simultaneously browsing the Internet through wireless link 703 to access point 716. The term simultaneously as used herein shall mean immediate or nearly immediate succession in time. In another embodiment, the connection from the mobile communication device to the memory storage 218 could be wired. Alternatively, the communication device could be simultaneously connecting to memory storage 218 while communicating with devices 706, 708 and 710 through wireless links 703. This pass through Internet feature allows the user to access data stored in the memory 218 and browse the Internet simultaneously from a single device (mobile communication device 300) or a plurality of devices. The WLAN modem 216 is designed to operate in one or more bands and cover one or more wireless standards. The bands may include first and second frequency bands (e.g., 2 GHz and 5 GHz). The WLAN modem 216 may use the first band for the transmission of information from memory storage 218 to the mobile communication device 300 and the second band for communications with the access point 716 (and thereby the Internet).

Figure 9:
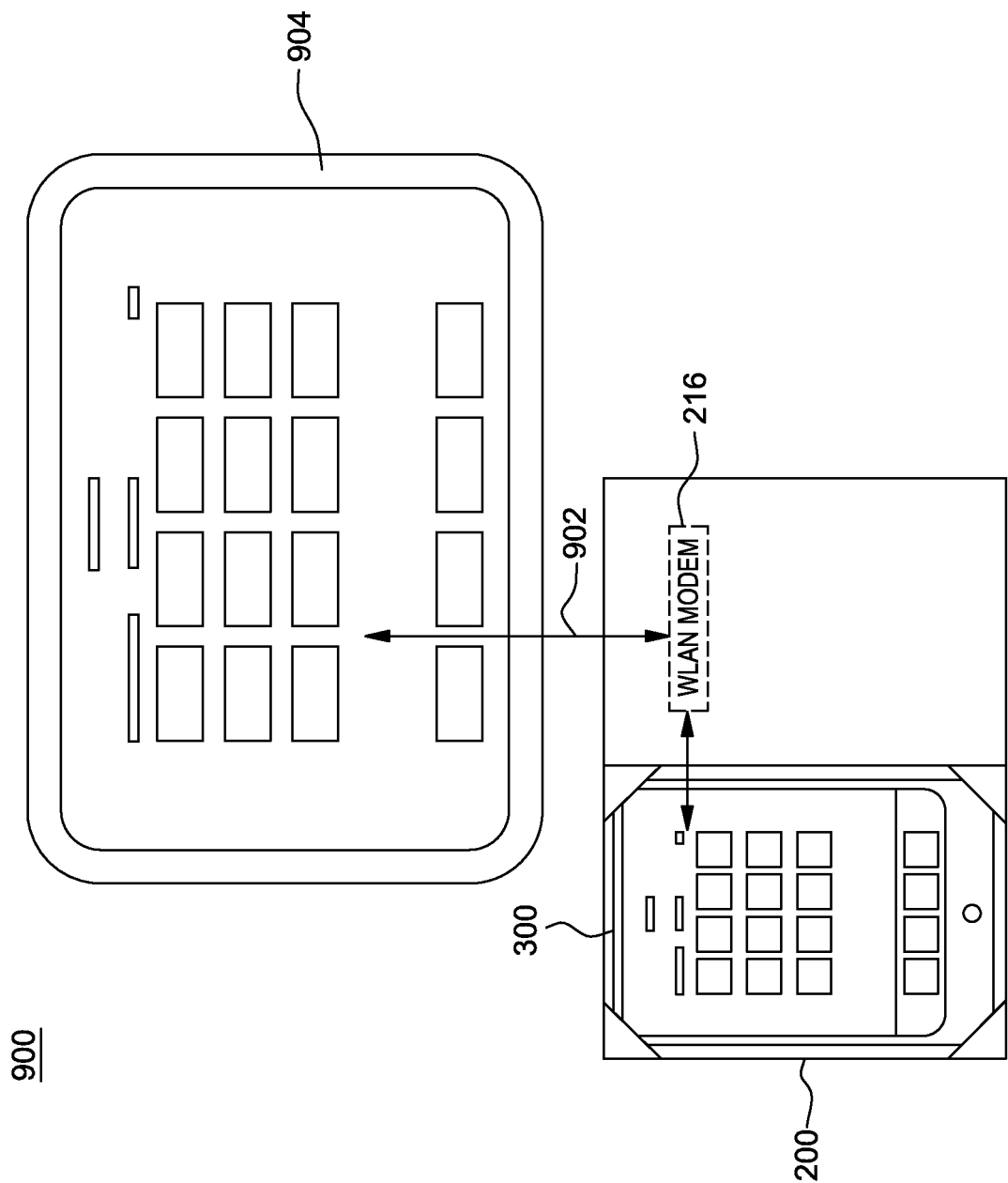
FIG. 9 is a view of the PCCC operating with a large external monitor.

FIG. 9 illustrates another environment 900 in which the PCCC 200 may operate. The PCCC 200 allows the mobile communication device 300 to link through WLAN 216 and wireless link 902 with large external monitor 904 using WiFi, SuperWiFi, WHDMI, or the like and display information (e.g., video, audio, or text) from either the mobile communication device 300, the memory storage or another source (e.g., devices 706, 708, 710) on to the monitor 904.

FIGS. 10-13B illustrate another environment 1000 in which the PCCC 200 may operate. As new wireless and fixed standards (such as 4G, 5G, 802.11ad, and the like) keep pushing the operating frequencies into millimeter (mm) wave spectrum (e.g., 28 GHz, 40 GHz, 60 GHz, 70 GHz, 100 GHz) it becomes harder and harder (due to higher penetration loss and path loss) to get the signal inside buildings, houses, cars, and even mobile phones (as phone casings might prevent millimeter wave signals from getting in or out). These challenges limit the usability of mm waves and make mm systems very expensive to deploy. The disclosed embodiments described herein help to make mm wave signal penetration possible.

In FIGS. 10-13B, PCCC 200 is an alternative embodiment in which an antenna array 240 is mounted in the case. (In alternative embodiments of FIGS. 10-13B it could be the one panel version of PCCC 500 shown in FIGS. 6A-6B used instead of the multiple panel version of the PCCC 200 but FIGS. 10-13B will use PCCC 200 for description purposes). PCCC 200 can be any of the embodiments disclosed in FIGS. 1-9 which either further include antenna array 240 or where antenna array replaces elements and or modules of the PCCC 200 (or PCCC 500) disclosed in FIGS. 1-9. Antenna 240 can be a low cost antenna array 240 made up of cells in an N×N array (e.g. 2×2, 2×2, 4×4, 8×8, or the like) or an M×N array (e.g., 1×4, 2×4, 2×5, 2×8, or the like). The antenna array 240 could be made on circuit boards 206 or 207, it could be a chip antenna on the circuit boards 206 or 207, or it could be a multilayer antenna on the circuit boards 206 or 207. The antenna array 240 can be used to increase the gain of the signal 1004, can be used for beam forming and beam steering, phase shifting, and/or gesture tracking. The antenna array 240 may be in contact with the mobile communication device (not shown) wirelessly, through physical contact or through a connector (e.g., 202b) or an electrical link (or links) running through circuit boards 206 and 207. In alternative embodiments, the antenna array 240 could be attached to the side or back of the mobile communication device (such as when it is the form of embodiment PCCC 500) as well. The antenna array 240 may also be coupled to and controlled by the other elements and modules in the PCCC 200 (or PCCC 500) through electrical links in the circuit boards 206 and/or 207 and implemented using hardware, software, firmware, middleware, microcode, or any combination thereof. Antenna array 240 may be configured in a plurality of ways. Antenna 240 may be made up of cells in an N×N or M×N array configuration as discussed above. The array 240 may made of a low-cost material and a number of different substrates could be used each having their own fabrication tolerances and electrical and mechanical properties. The array 240 can be made of an Anion CLTE-XT (PTFE ceramic), a Rogers RT 5880/RO 3003 (PTFE glass fiber), a Rogers Liquid Crystal Polymer (LCP), a low temperature cofired ceramic (LTCC), a Parylene N dielectric, a polytetrafluoroethylene (PTFE) ceramic, a PTFE glass fiber material, a silicon material, a Gallium Arsenite (GaAs) material, an Alumina material, a Teflon material, a Duroid material or any other material that can produce thin (about 2-4 mils in thickness) metallized layers. In one embodiment, the layers may be stacked to form a multi-layer array architecture. With the antenna array 240 printed on a thin film material, mm wave signals can penetrate through any object efficiently and at low cost. The PCCC 200 surrounding array 240 may also be made of glass, plastic, etc.

Figure 10:
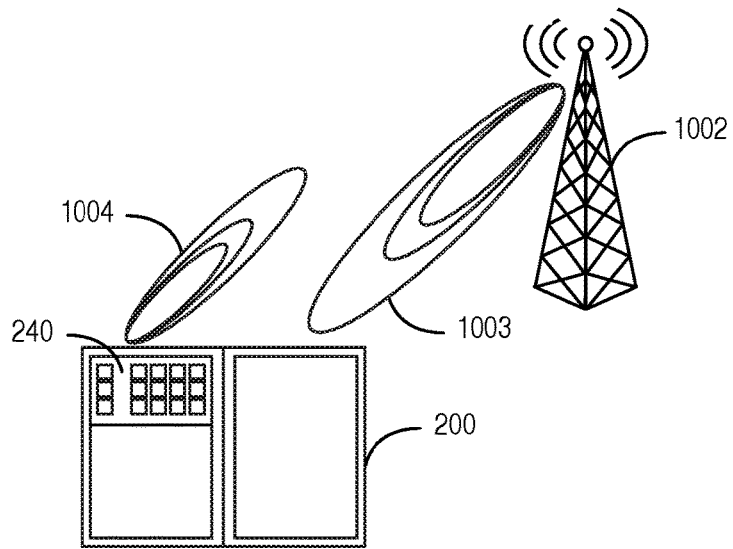
FIG. 10 is a PCCC 200 with an antenna array 240 in communication with a communication tower (e.g., cell tower, base station or the like) 1002 using millimeter (mm) wave signals 1003, 1004.

In FIG. 10, in operating environment 1000 antenna array 240 allows PCCC 200 to communicate with a communication tower (e.g., cell tower, base station or the like) 1002. Communication tower 1002 and antenna array 240 could communicate with each other using, for example, time domain (TDD) or frequency domain signals (FDD) 1002, 1003 (and 1302 as discussed below). Downlink signal (or beam) 1003 coming from communication tower 1002 and uplink signal (or beam) 1004 coming from array 240 are formed and steered to allow mm wave signal communications between the array 240 and communication tower 1002. The antenna array 240 may be located by communication tower 1002 using Global Positioning Satellite (GPS) technology or by 3G/4G/5G technology. Beams 1003 and 1004 (and 1302) may operate in the range of approximately 3 GigaHertz (GHz) to approximately 100 GHz or even higher. Typically, beams 1003 and 1004 (and 1302) will operate approximately in a range of plus or minus (+/−) 12% of mm wave frequency signals such as 24 GHz, 28 GHz, 39 GHz, 60 GHz, and/or 77 GHz (e.g., for 24 GHz the signal would range from approximately 21.12 GHz to approximately 26.88 GHz). Alternatively, mm wave beams 1003 and 1004 (and 1302) can operate in the following ranges: approximately 3.3 GHz to approximately 3.4 GHz; approximately 3.4 GHz to approximately 3.6 GHz; approximately 3.6 GHz to approximately 3.8 GHz; approximately 5.150 GHz to approximately 5.925 GHz; approximately 24.25 GHz to approximately 27.5 GHz; approximately 31.8 GHz to approximately 33.4 GHz; approximately 37.0 GHz to approximately 40.5 GHz; approximately 40.5 GHz to approximately 42.5 GHz; approximately 42.5 GHz to approximately 43.5 GHz; approximately 45.5 GHz to approximately 47 GHz; approximately 47.0 GHz to approximately 47.2 GHz; approximately 47.2 GHz to approximately 50.2 GHz; and approximately 50.4 GHz to approximately 52.8 GHz.

Figure 11:
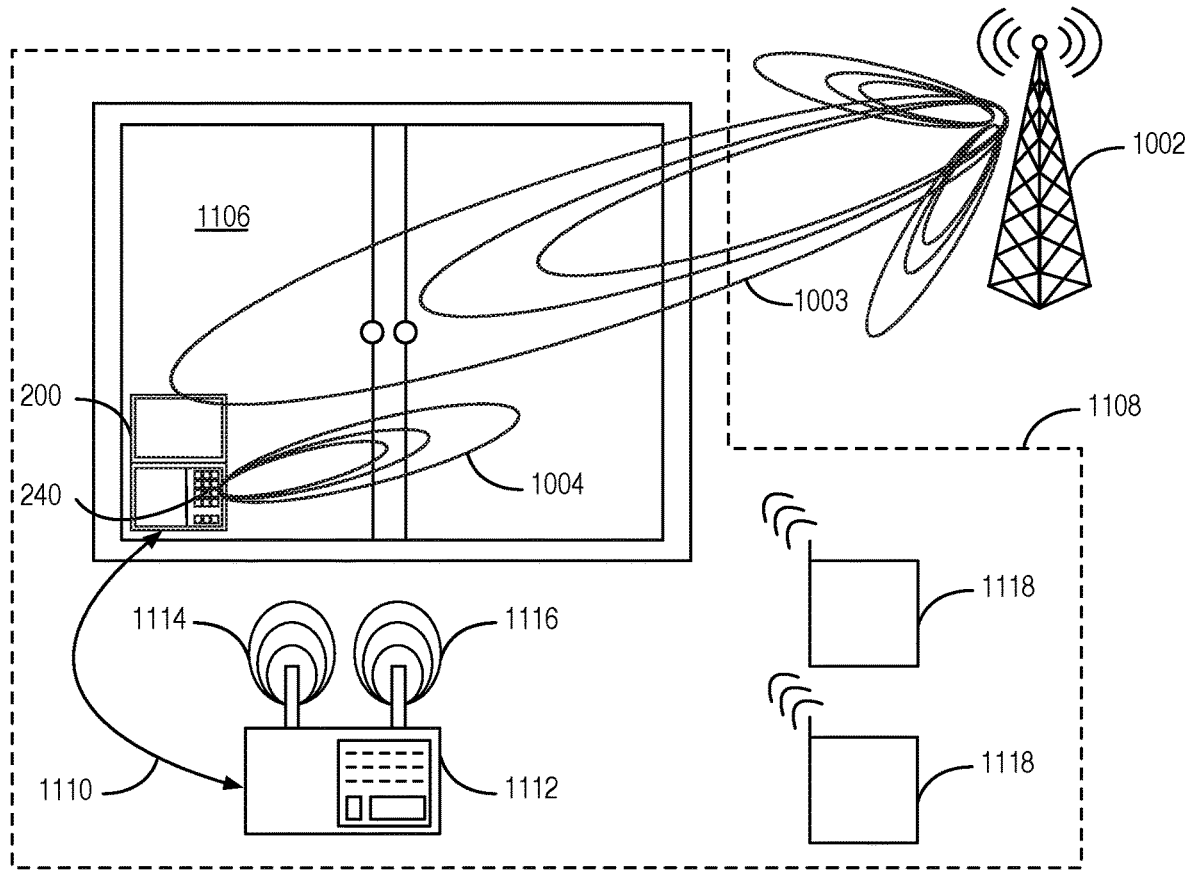
FIG. 11 illustrates an environment in which a communication tower 1002 communicates through downlink signal 1003 and uplink signal 1004 back and forth in mm wave signals between a PCCC 200 with an antenna array 240 mounted on a window 1106 inside a building 1108.

FIG. 11 shows an alternative operating environment 1100 in which a communication tower 1002 communicates through downlink signals (or beams) 1003 and 1004 back and forth in mm wave signals with a PCCC 200 (or PCCC 500) with an antenna array 240 mounted on a window 1106 inside a building 1108 (or outside the building, e.g., resting on a ledge). PCCC 200 may be mounted to window 1106 through adhesives such as suction cups or through some other type of mounting mechanisms. The mm waves 1003 sent from communication tower 1002 can be received at PCCC 200. PCCC 200 could then down convert the mm wave signals 1003 using other modules in the case 200 to lower frequency signals (e.g., approximately 2 GHz, 5 GHz, 8 GHz or the like). In some embodiments, these lower frequency signals are forwarded from a connection on the case 200 (e.g., 202b) through a wired coupling (e.g., a cable) 1110 to user equipment device (or a plurality of user equipment devices) 1112. PCCC 200 can also send signals wirelessly to user equipment device 1112 (e.g., using 802.11ad and/or 802.11ax). User equipment device (UED) 1112 located in the building 1108 has the ability to forward the signal through UED signals 1114 and 1116 (which typically are at different frequencies such as WiFi, Bluetooth, Zigbee, etc.) to a plurality of devices 1118 such as phones, tablets, and/or televisions. Wired coupling 1110 not only carries the RF signals received and sent to and from the antenna array 240 but it may also provide control signals and power supply for the antenna array 240. The cable 1110 can typically carry frequencies for example from approximately 0to 8 GHz. The cable 1110 can be short or long. The UED 1112 has the processing power (i.e., CPU, baseband, modem, etc.) to handle the received signal and send signals to and from the antenna array 240. It also may contain communication modules such as WiFi radio, LTE/LTE-AiLTE-U/LAA, and/or Zigbee. The UE 1112 can act as a small cell or WiFi Access Point. The UE 1112 can contact the user to the outside communication tower 1002 through the antenna array 240.

Figure 12:
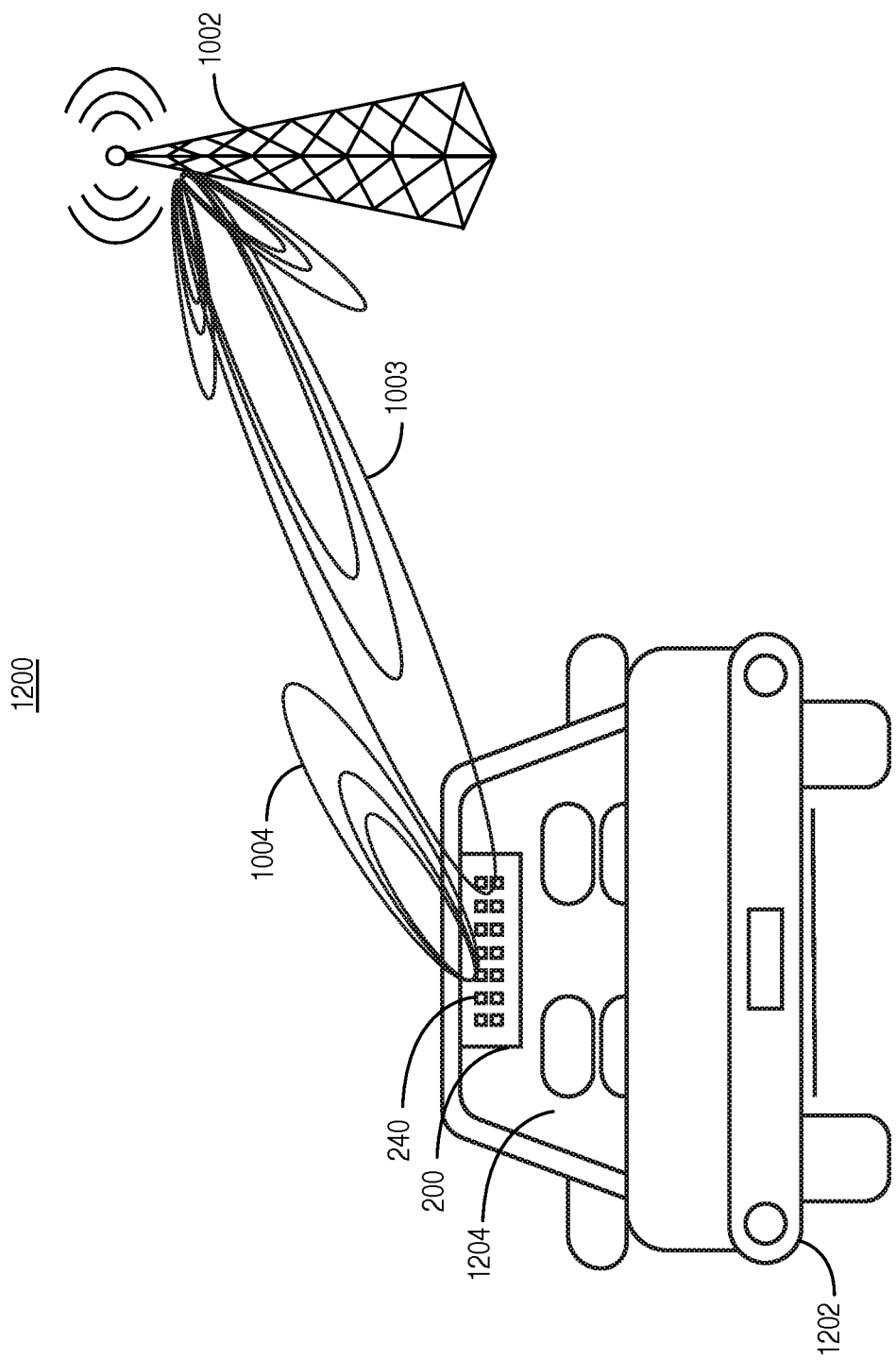
FIG. 12 shows an operating environment 1200 in which a communication tower 1002 communicates through mm wave signals 1103 and 1104 back and forth to and from a PCCC 200 with an antenna array 240 mounted in a vehicle 1202 on the glass 1204 through an adhesive.

FIG. 12 shows an alternative operating environment 1200 in which a communication tower 1002 communicates through mm wave signals 1003 and 1004 back and forth with a PCCC 200 (or PCCC 500) with an antenna array 240 mounted in a vehicle 1202 on the glass 1204 through an adhesive such as suction cups. Alternatively, the glass 1204 could be manufactured with the components of the PCCC 200 (or PCCC 500) built in.

Figure 13A:
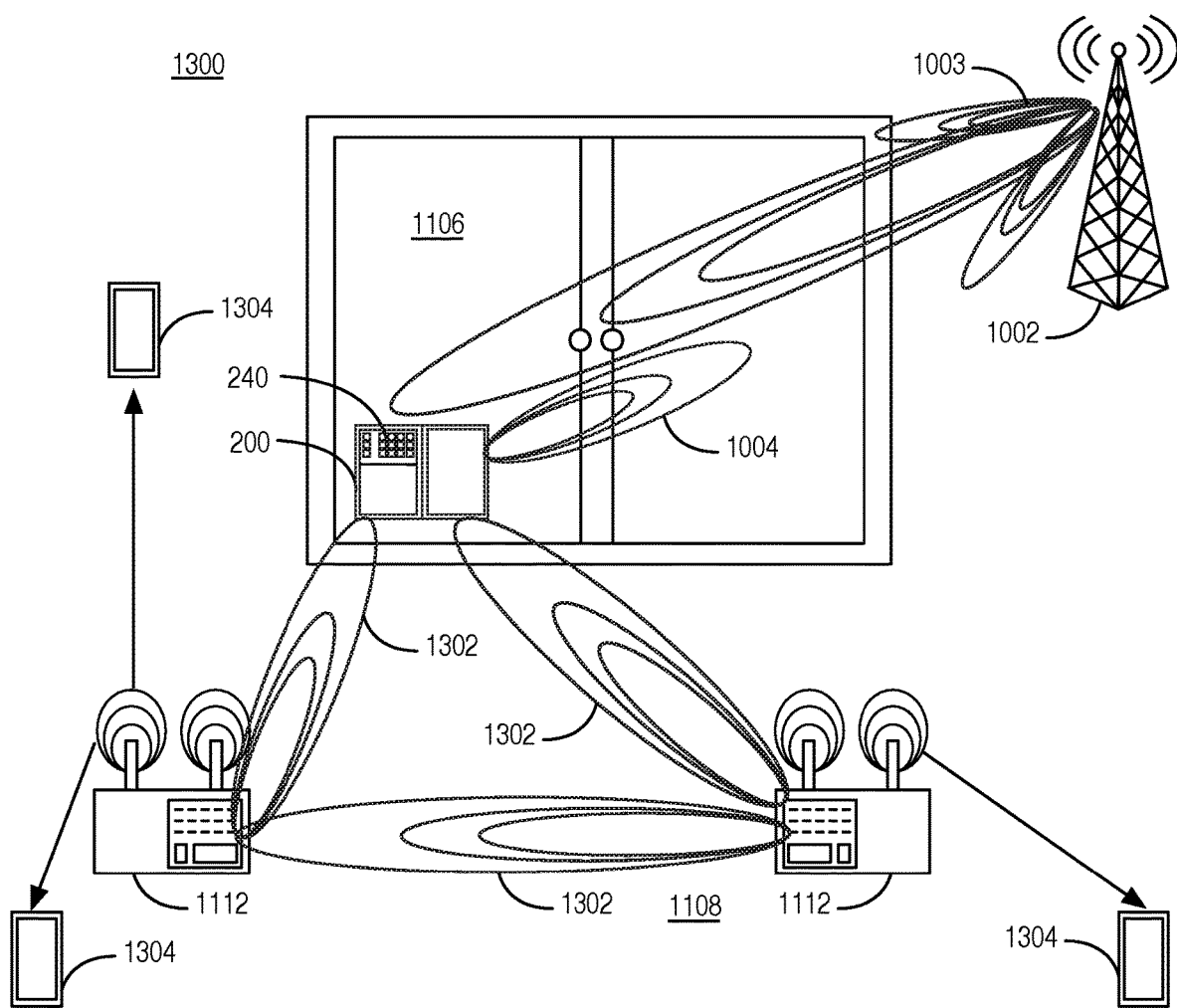
FIG. 13A shows an operating environment 1300 in which user equipment device 1112 has a PCCC 200 (e.g., mounted or integrated) so that PCCCs 200 can communicate with each other wirelessly using mm waves 1302
Figure 13B:
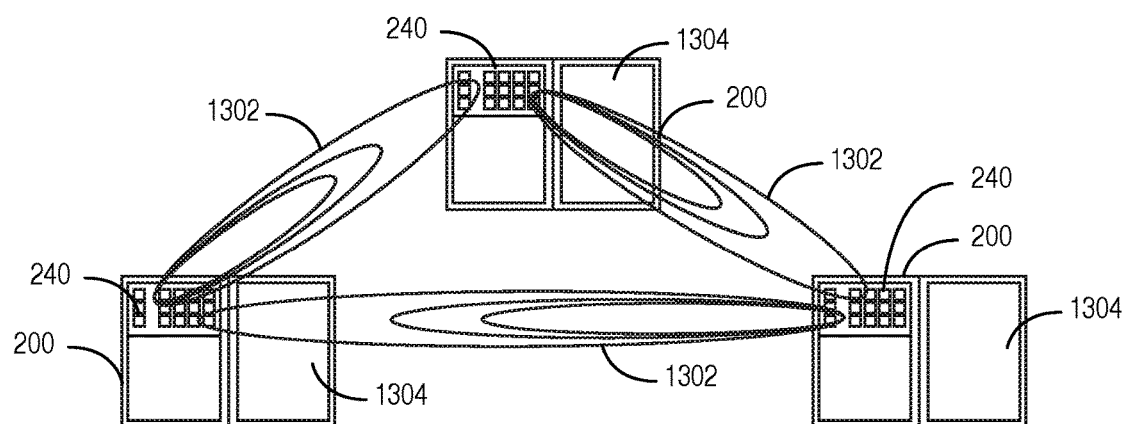
FIG. 13B illustrates a phone 1304 physically connected with a PCCC 200 (e.g., mounted or integrated) so that two PCCCs 200 can communicate with each other wirelessly.

FIG. 13A shows an alternative operating environment 1300 in which user equipment 1112 can further have a PCCC 200 mounted or integrated so that PCCCs 200 (or 500) (in this case 3 PCCCs) can communicate with each other wirelessly using mm waves 1302. A first PCCC 200 could communicate with a plurality of PCCCs 200 at the same time or different times using beam forming, multiple input/multiple output (MIMO), massive MIMO, or the like. UED 1112 can then turn the mm waves 1302 in order to wirelessly communicate with mobile communication devices such as phones, tablets, etc. 1304. In FIG. 13B a phone 1304 can have a PCCC 200 (or 500) connected (e.g., mounted or integrated), so that 2 PCCCs 200 could communicate with each other wirelessly for device to device communication. One PCCC 200 could communicate with a plurality of PCCCs 200 at the same time or different times using mm waves 1302 with beam forming, MIMO, massive MIMO, or the like.

Figure 14A:
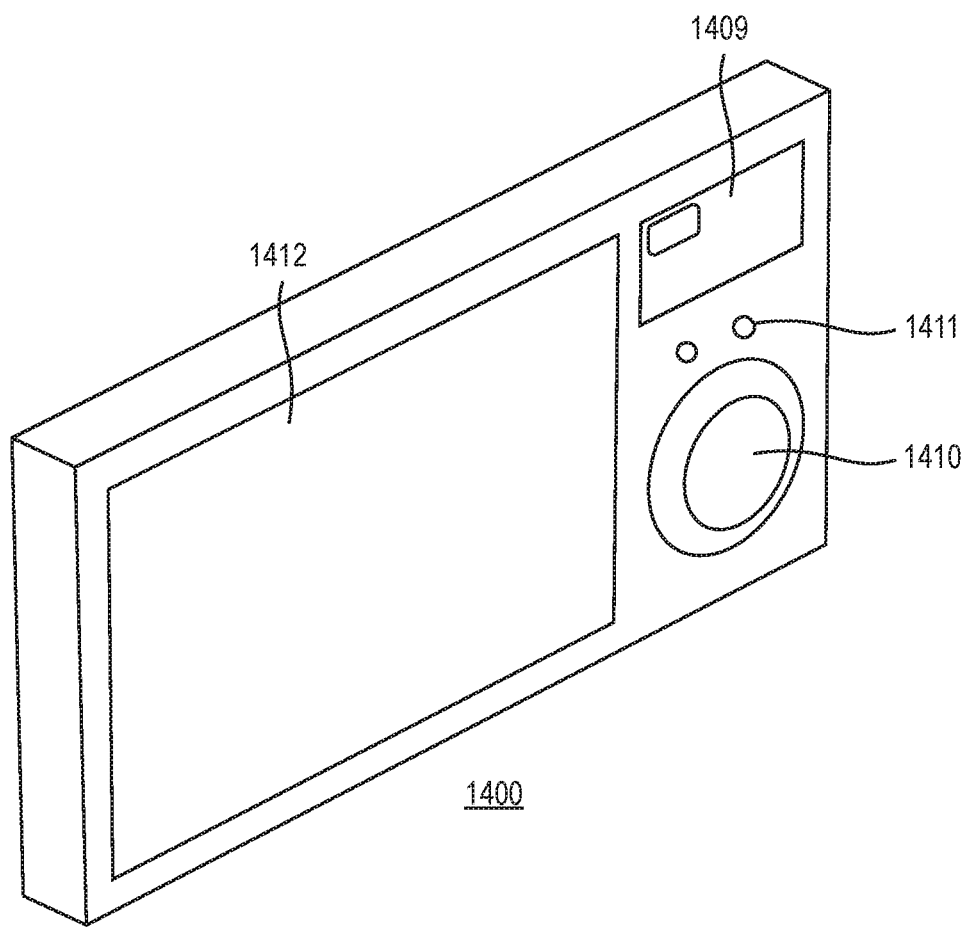
FIG. 14A is an Instant Direct Wireless Communication Device ("communication device") 1400 capable of forming instantaneous networks.

FIG. 14A is an exemplary wireless communication device ("communication device") 1400 capable of forming instantaneous networks (which is referenced as 1500 herein). A first communication device 1400 is capable of transmitting and receiving RF signals (including WiFi signals) "directly" to a single, second wireless communication device 1400 of a plurality of wireless communication devices 1400 or directly to a plurality of wireless communication devices. The terms "direct" or "directly" shall mean for purposes of this disclosure that the signal between two communication devices does not go through the fixed base station infrastructure. The first communication device 1400 will typically be "proximate" to a second communication device 1400. The terms "proximate" or "proximately" shall mean for the purposes of this disclosure shall mean nearness in physical space. The limitations on the distance between the first and second communication devices may be user definable and/or frequency limited. Therefore, the distance between first and second communication devices may be in the range of one foot to ten miles. For example, the distances might be approximately, 1 foot, 10 feet, 100 feet, 1000 feet, 1 mile, and 10 miles. In alternative embodiments, the first wireless communication device 1400 can communicate through the fixed base station infrastructure and communicate with a second wireless communication device (or communication devices) 1400 using 3G, 4G, and/or 5G.

Figure 14B:
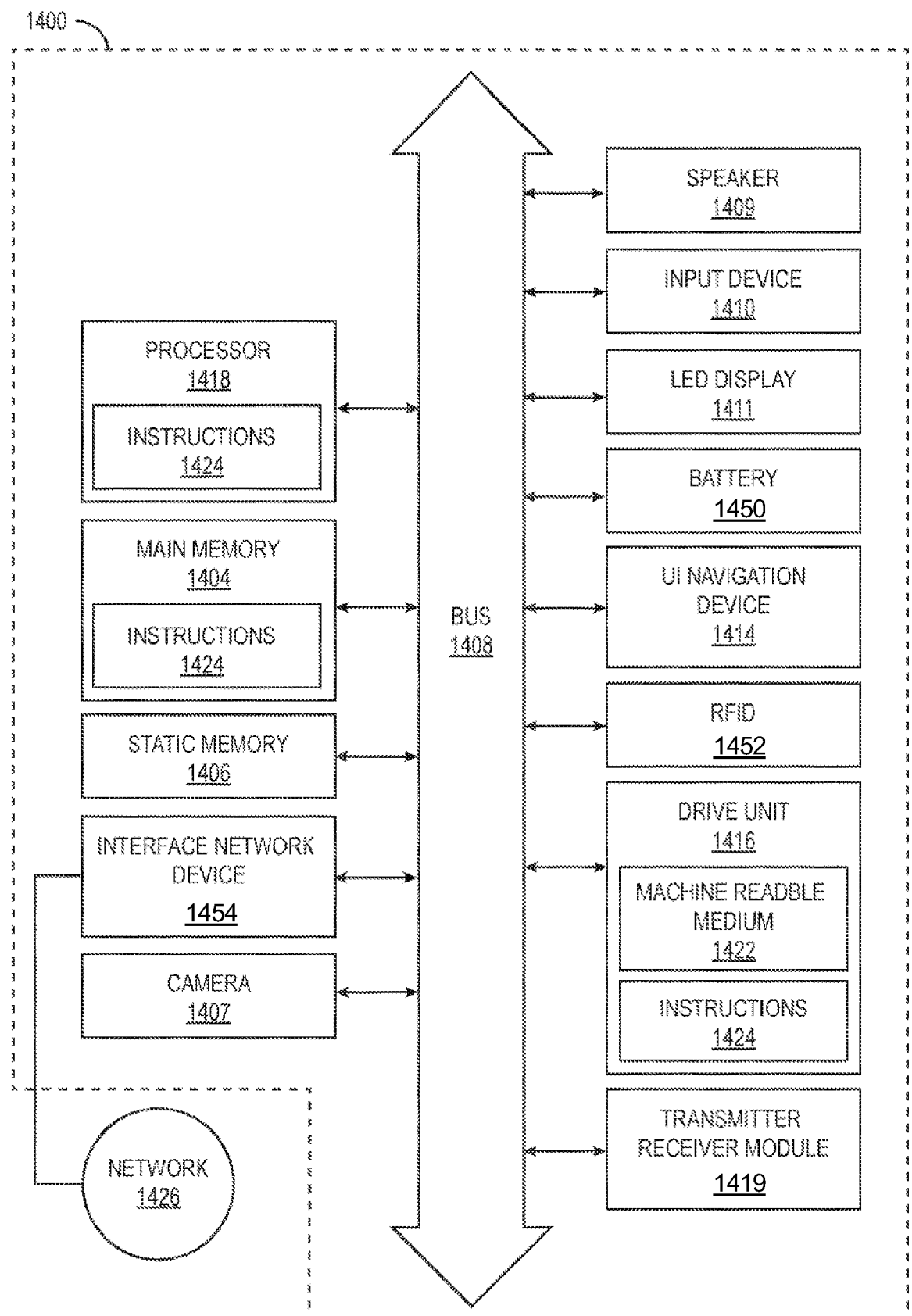
FIG. 14B is a block diagram illustrating components of the communication device 1400.

FIG. 14B is a block diagram illustrating components of the communication device 1400. The communication device 1400 is able to able to read instructions from a machine-readable medium (e.g., a machine-readable storage medium) and perform any one or more of the methodologies discussed herein. Specifically, FIG. 14B shows a diagrammatic representation of the communication 1400 device in the form of a computer system and within which instructions 1424 (e.g., firmware or software) for causing the communication device 1400 to perform any one or more of the methodologies discussed herein may be executed. Communication devices 1400 may operate as peer machines in a peer-to-peer (or distributed) network environment. The communication device 1400 may be a dedicated device or, in alternative embodiments, may be an application (1413) running on a smartphone, tablet, computer or other device which has wireless communication capabilities and is capable of executing the instructions 1424, sequentially or otherwise, that specify actions to be taken by that communication device 1400. Further, while only a single communication device 1400 is shown in FIGS. 14A and 14B, the instantaneous network described herein will typically operate as a plurality of wireless communication devices to perform any one or more of the methodologies discussed herein.

The communication device 1400 includes a processor (or processors) 1418 (e.g., a central processing unit (CPU), a graphics processing unit (GPU), a digital signal processor (DSP), an application specific integrated circuit (ASIC), a radio-frequency integrated circuit (RFIC), or any suitable combination thereof), a main memory 1404, and a static memory 1406, which are configured to communicate with each other via a bus 1408. The communication device 1400 may include an input device 1410 which may be as simple as a button. In operation, the input device 1410 may be pushed to start the connection process with a second wireless communication device 1400. The input device 1410 may work with the LED displays 1411 to indicate when a connection is made. The communication device 1400 may further include a display screen 1412 (e.g., a plasma display panel (PDP), a light emitting diode (LED) display, organic LED, microLED, a liquid crystal display (LCD)). The display screen 1412 may have a touch screen, be controlled by a user interface navigation or cursor control device 1414 (e.g., a mouse, a touchpad, a trackball, a joystick, a motion sensor, or other pointing instrument), controlled through eye tracking technology by the operator and/or controlled by physical gestures of the operator. As will be discussed below, the display screen 1412 may display selectable icons and avatars overlayed on a map to show their locations. An "icon" shall be a figure or symbol representing a wireless communication device 1400 and/or operator and an "avatar" is a graphical representation of the operator or a character representing the operator. Both icons and avatars are referenced herein as 1440 and will be used interchangeably. These icons 1440 may be selected by touch by the operator to establish a communication link between the communication devices 1400. In an alternative embodiment, an artificial intelligence (AI) program such as a machine learning program stored in memory 1404 may be used in the identification and selection of icons and avatars 1440 to form a communication link. Machine learning allows a machine to learn on its own without being explicitly programmed. This application of AI/machine learning provides the wireless communication devices 1400 the ability to automatically learn and improve from experience.

The communication device 1400 may further include a battery 1450, a camera 1407 (which may be used in video communications to show the face of the operator and/or monitor the eyes of the operator through eye tracking), and speaker and microphone 1409. The speaker and microphone 1409 may be used to communicate with other wireless communication devices 1400 and also may be used to control the wireless communication device through voice commands. An RF identification (RFID) chip 1452 may be used to send out an identification signals to other wireless communication devices as part of a handshake process. A storage unit 1416 includes a machine-readable medium 1422 on which is stored the instructions 1424 (e.g., firmware or software) embodying any one or more of the methodologies or functions for operation of the instantaneous network 1500 described herein. The instructions 1424 may also reside, completely or at least partially, within the main memory 1404, within processor 1418 (e.g., within the processor's cache memory), or both, during execution thereof by the communication device 1400. Accordingly, the main memory 1404 and processor 1418 may be considered as machine-readable media. The instructions 1424 may be transmitted or received over a network 1426 via network interface device 1454.

As used herein, the term "memory" refers to a machine-readable medium able to store data temporarily or permanently and may be taken to include, but not be limited to, random-access memory (RAM), read-only memory (ROM), buffer memory, flash memory, and cache memory. While the machine-readable medium 1422 is shown in an example embodiment to be a single medium, the term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., software) for execution by the communication device 1400, such that the instructions, when executed by one or more processors of the machine (e.g., processor 1418), cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" shall accordingly be taken to include, but not be limited to, one or more data repositories in the form of a solid-state memory, an optical medium, a magnetic medium, or any suitable combination thereof.

Substantial variations may be made in accordance with specific requirements to the embodiments disclosed. For example, customized hardware might also be used, and/or particular elements might be implemented in hardware, software (including portable software, such as applets, etc.), or both.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information.

Figure 14C:
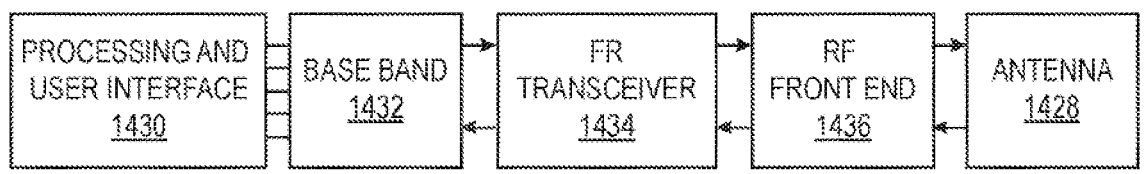
FIG. 14C shows a block diagram of the module 1419.

FIG. 14B further includes a transmitter and receiver module 1419. FIG. 14C shows a block diagram of the module 1419. Module 1419 is a set of mobile device components that convert information into radio signals that can be transmitted and received over the air. The radio frequency front end (RFFE) components of the module 1419 work in conjunction with the communication device's modem and antenna 1428.

As shown in FIG. 14C module 1419 which includes Processing & User Interface 1430 which is made up of a Computer Processing Unit (CPU), Application Processor, Graphics Processing Unit (GPU), Memory, LCD Drivers, Camera Sensors, Audio/Video Controller and other processing interfaces. Base Band 1432 performs signal processing and real-time radio transmission operations. Multi-mode, multi-band RF transceiver 1434 performs conversions between digital baseband and analog RF signals. RFFE 1436 contains active and passive components for RF transmission/reception such as power amplifiers, filters, switches, duplexers, diplexers, and low-noise amplifiers (LNAs). Antenna 1428 can be a multi-mode, multi-band antenna.

Figure 15A:
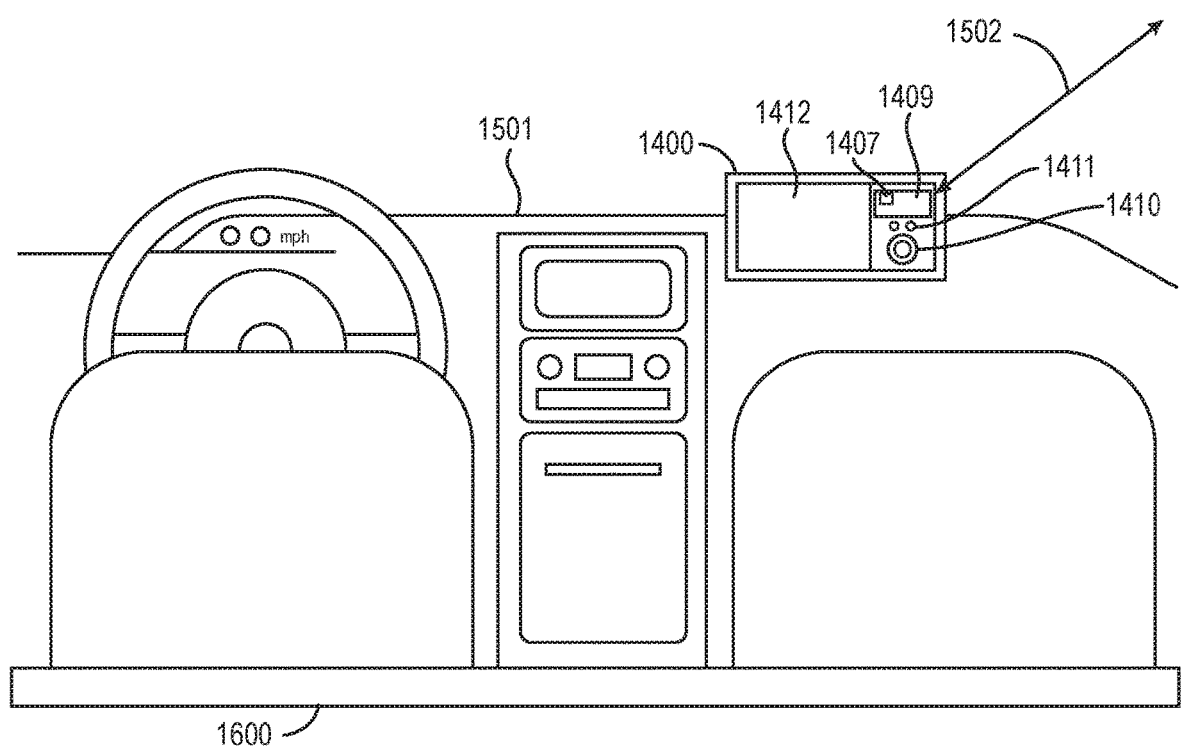
FIGS. 15A and 15B show the implementation of an instantaneous communication system and method 1500 with a communication device 1400 mounted on a dashboard 1501 inside a vehicle 1600.
Figure 15B:
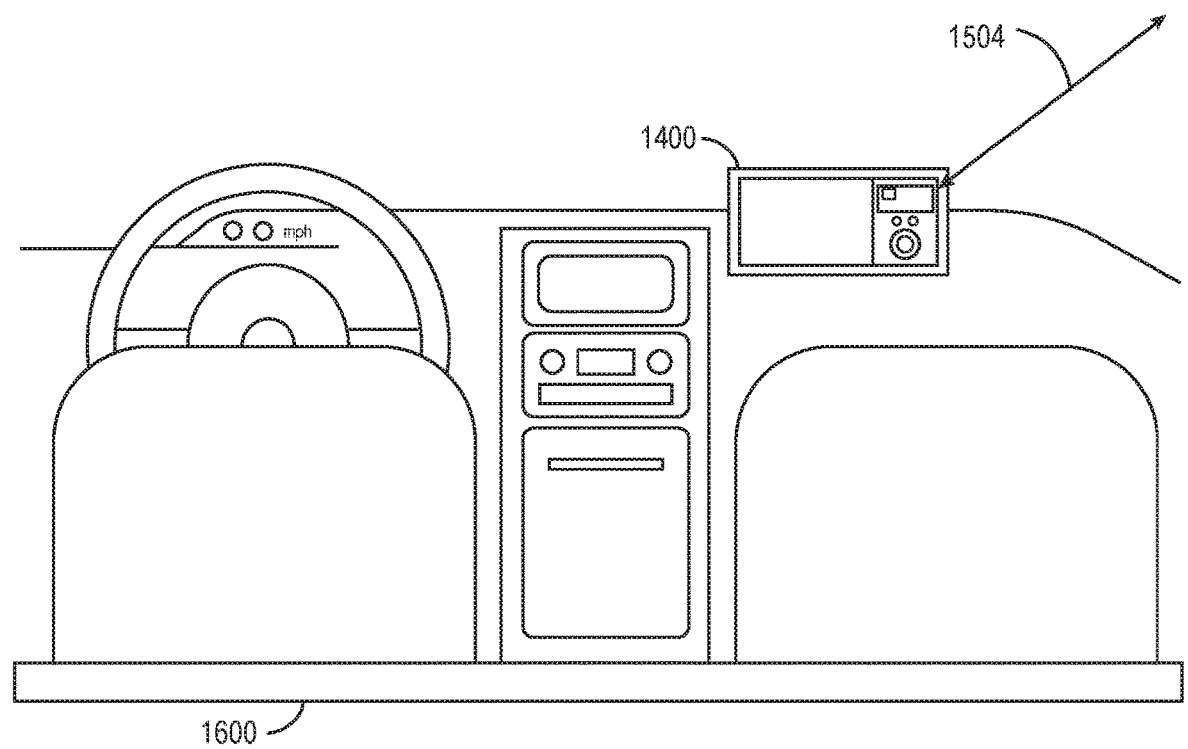

FIG. 15A shows an instantaneous communication network system and method 1500 formed by a communication device 1400 mounted on a dashboard 1501 inside a vehicle 1600. The instantaneous communication network system and method 1500 will function in many aspects as an intercom system and will be referred to in those terms alternatively throughout this disclosure. A standalone communication device 1400 may be placed inside vehicle 1600 (e.g., on dashboard 1501) and can be charged using the battery (not shown) of the vehicle 1600. The communication device 1400 may use short range communication technologies (e.g., WiFi, Bluetooth, Zigbee, intercom protocol), camera 1407, speaker 1409, and visual indication display screen 1412. An application 1413 which is stored in memory 1404 and/or unit 1416 may control operation of the communication device 1400, the display screen 1412 and the interactions of the operator with the display screen (e.g., touch screen entries by operator may be enabled by application 1413 in certain embodiments). FIG. 15A shows wireless communications 1502 within or nearby the vehicle 1600. In alternative embodiments, the device 1400 can also have long range communication technologies (e.g., cellular, 4G, 5G, 5G new radio (NR), stand alone (SA) 5G, nonstand alone (NSA) 5G). FIG. 15B shows long distance communication 1504 (which in some non-direct embodiment may be with a base station). The device 1400 may run on Android, Windows, or iOS.

Figure 15C:
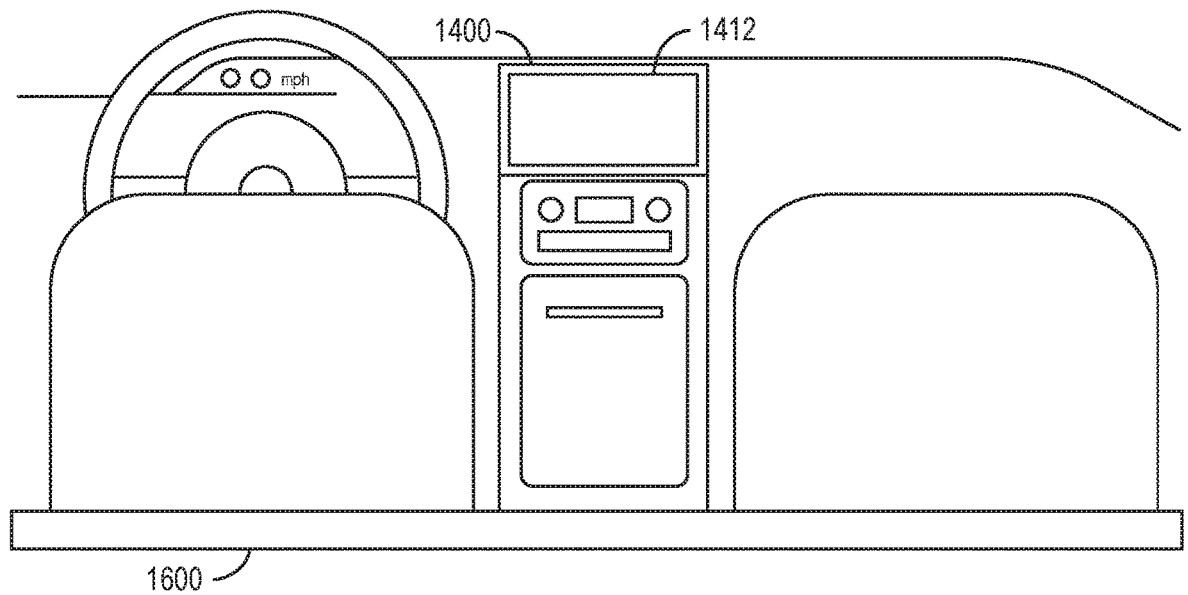
FIG. 15C shows communication device 1400 built into the dashboard 1501 of the vehicle 1600 which allows for a larger display screen 1412 and other features.

FIG. 15C shows communication device 1400 built into the vehicle 1600 which allows for bigger display screen 1412 and other features.

Figure 15D:
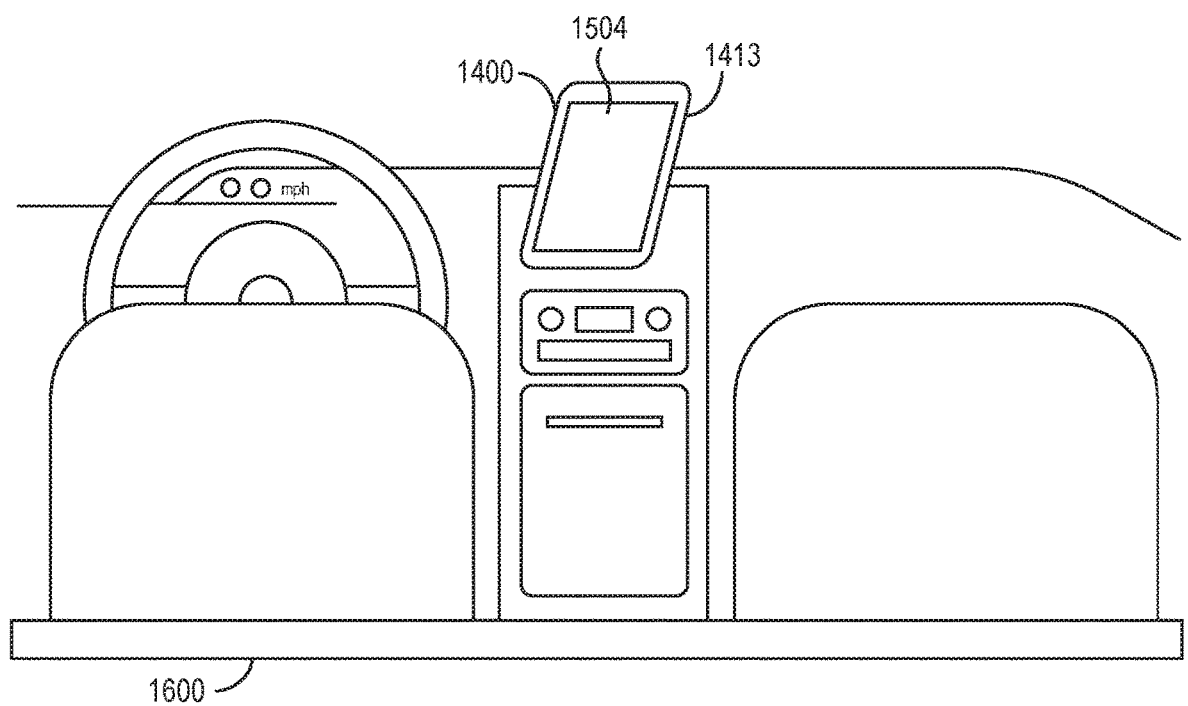
FIG. 15D shows that instead of a standalone communication device 1400, the communication device 1400 may be a smartphone, wireless tablet, or computer and may used to implement the instant communication network using an application 1413

FIG. 15D shows that instead of a standalone communication device 1400, the communication device 1400 may be a smartphone, wireless tablet, or computer and may be used to implement the instant communication network 1500 using application 1413 which is stored in the memory of the smartphone, tablet or computer. The operating system for device 1400 in this embodiment may be Android Auto, Apple Carplay, Windows, and Ford Sync. The application 1413 may utilize the device's 1400 hardware, such as WiFi, GPS, 4G, 5G, Bluetooth, speakers, camera, and screen.

Figure 15E:
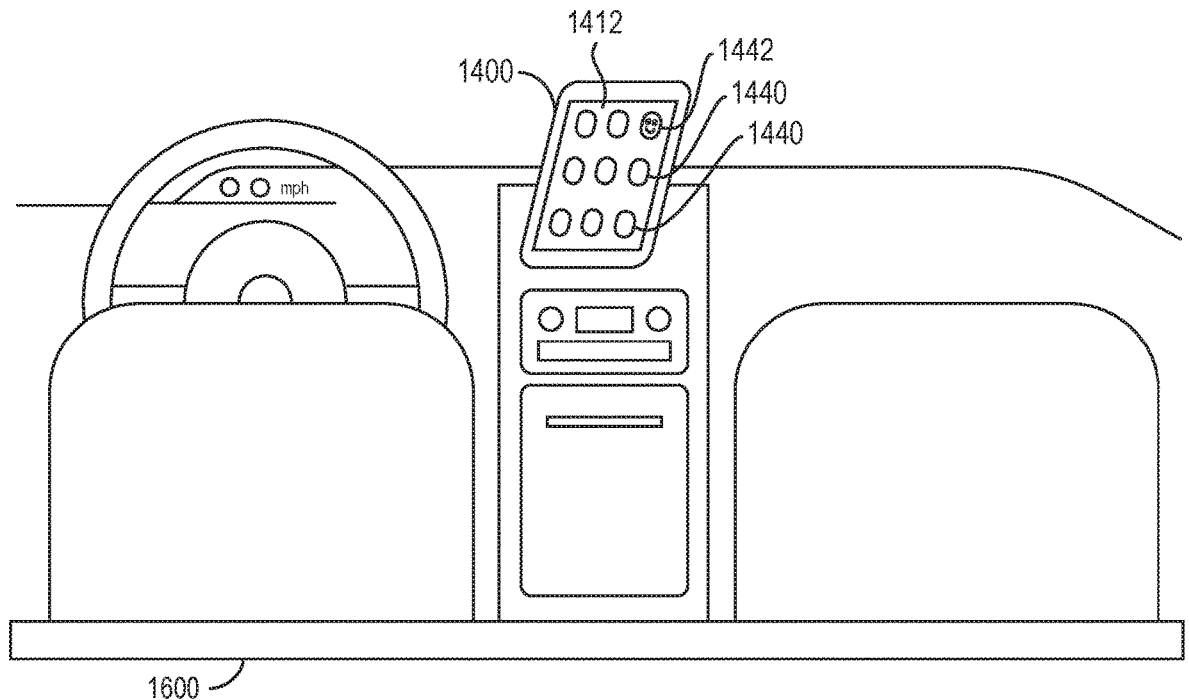
FIG. 15E shows a detailed view of the display screen 1412 of communication device 1400.

FIG. 15E shows a detailed view of the display screen 1412 of communication device 1400. The application 1413 can utilize and interact with other applications such as Waze, Line, Viber, WhatsApp, Zoom, and Skype to locate the nearest icon or avatar 1440 that represents a vehicle 1600, another communication device 1900 associated with an operator (but not mounted in a vehicle), or a building 1902. Once the desired vehicle 1600, device 1900 or building 1902 has been located, the operator may click on the icon or avatar 1440 for the vehicle 1600, device 1900 and building 1902 and may talk to the other party over a communication link. In one embodiment, the communication link is a direct link without using a fixed base station infrastructure. In other embodiments, the communication link will be through the fixed base station infrastructure. In one embodiment, the communication link may function as an intercom. The application 1413 shows all the vehicles 1600, devices 1900, and buildings 1902 surrounding the vehicle 1600 (i.e., proximate to the vehicle) that are within range to communicate (as icons or avatars 1440). The range may be a predetermined range set by the operator. In alternative embodiments, the range may be the limits on the predetermined frequency selected by the operator. The icons or avatars 1440 may indicate if a person is willing to talk, listen or wish to not be disturbed through the use of emojis 1442 which communicate the desires or feelings of the operator of a wireless communication device 1400. The operator of the communication device may simply click on the icon 1440 associated with the person and choose to talk, to listen, broadcast a message, send an emoji 1442, share music, or listen to the same radio station. The operator of application 1413 may ask for directions or restaurant recommendation. The application 1413 can also have credentials for different operators. For example, businesses can have their real names displayed on the application 1413 with name being accredited by the application 1413, the operator can be anonymous, the operator can display a real name, or the operator can use a different avatar name. The application 1413 can use voice controls to safely operate such as Alexa and Google assistant.

Figure 15F:
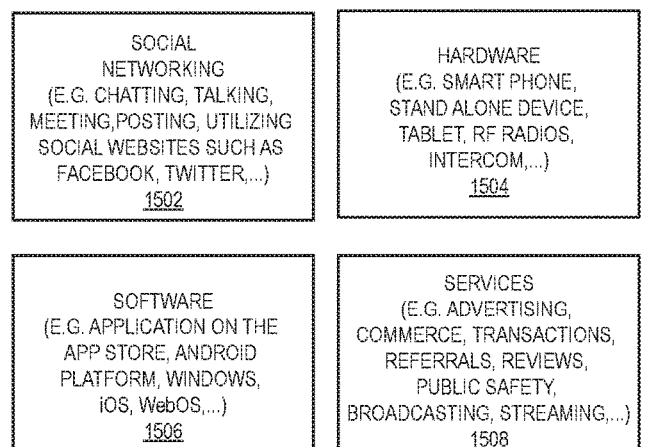
FIG. 15F shows a block diagram outline of an instantaneous direct communication network system and method 1500 made up of a plurality of communication devices 1400.

FIG. 15F shows a block diagram outline of the instantaneous direct communication network system and method 1500 made up of a plurality of communication devices 1400. The network 1500 has the following four components: a social network 1502, hardware 1504, software 1506 and services 1508. The social network 1502 may be based on proximity of communication devices 1400. As discussed above, the communication devices 1400 may be mounted in vehicles 1600, associated with persons, or with buildings. The instantaneous network 1500 may be achieved by using any wireless communication standard (such as 3G, 4G, 5G, WiFi, Zigbee, ultra high frequency (UHF), Internet of Things (IOT) (including Industrial IOT)) on any radio frequency (e.g., 20 MHz-100 GHz) on any software platform (e.g., Android®, Windows®, webOS, and iOS). Fifth Generation (5G) wireless refers to a 3GPP telecommunication standard to replace the current fourth generation (4G) telecommunication standard. The 5G standard uses a frequency spectrum with high frequency/short wavelength, for example in the range of 400 MHz-100 GHz, with wavelengths in the range of 5 millimeters (mm) to 15 mm.

The instantaneous network 1500 allows people to socialize, visualize and interact with people in their close proximity using instantaneous connection technology. The instantaneous network 1500 allows for a new form of instantaneous commerce, such as targeted advertisement based on the location and the proximity of the people to the business. The social network 1502 allows for a more targeted public safety announcements based on the location and the proximity (e.g., Amber Alerts). The social network 1502 may allow for chatting, talking, meeting, posting, and utilizing social websites (e.g., Facebook, Twitter). The social network 1502 may be implemented on hardware 1504 such as smart phones, wireless tablets, RF radios, and intercoms. Software 1506 used to implement the social network 1502 may be applications from the Apple App Store, Android platform, Windows, iOS and WebOS. Services 1508 on the network 1500 may include advertising, commerce, transactions, referrals, reviews, public safety broadcasting and streaming.

Figure 16:
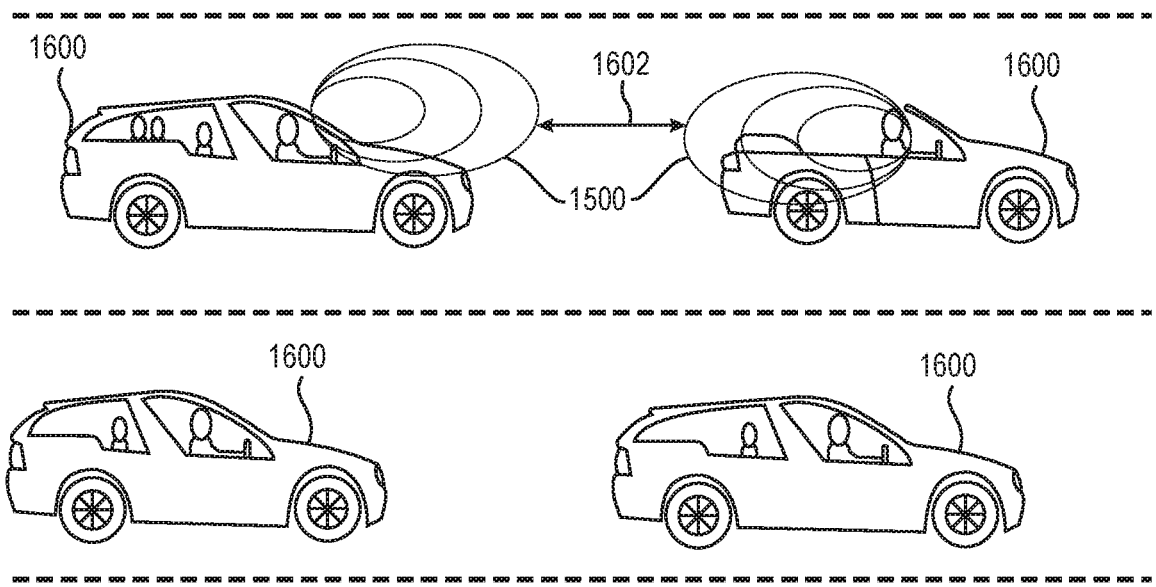
FIG. 16 shows vehicles 1600 forming a communication network 1500.

FIG. 16 shows vehicles 1600 forming an instantaneous communication network 1500. Two way communication is formed between two of the vehicles 1600 which are in range. A secure short range peer to peer "direct" communication link 1602 is formed which is similar to an intercom type channel. The network 1500 allows drivers in the vehicles 1600 to talk, listen to other conversations, not talk and only listen, and/or broadcast message to other vehicles 1600 in their range.

Figure 17:
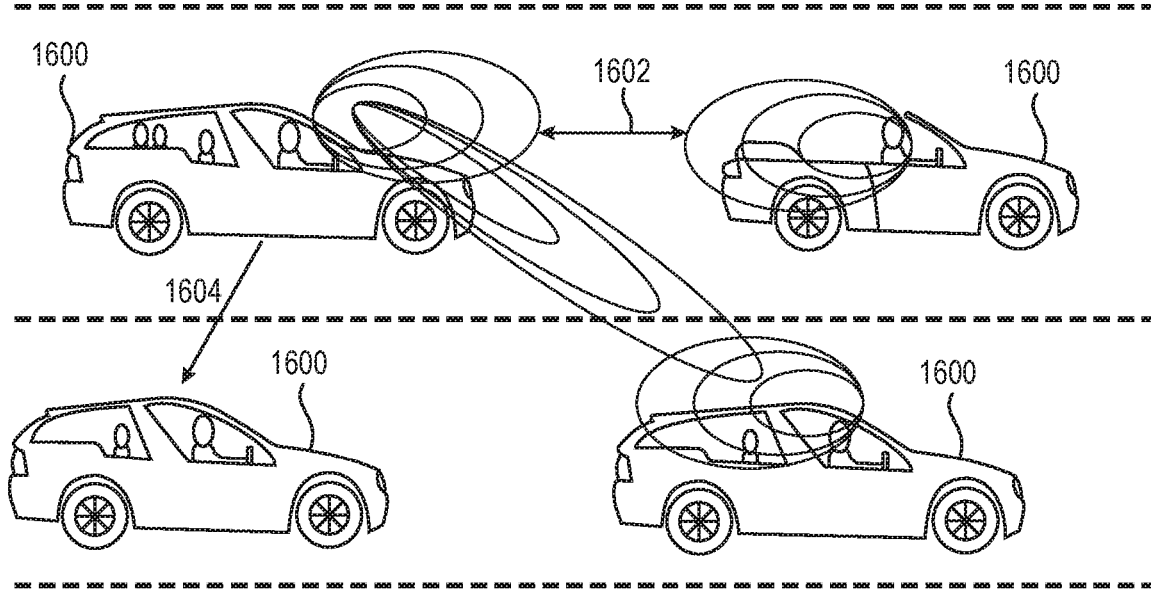
FIG. 17 shows a multi way communication network formed when vehicles 1600 are in range.

FIG. 17 shows a multi way communication network formed when a plurality of vehicles 1600 having communication devices 1400 are within range of each other. Not only is there a peer to peer communication link 1602 in FIG. 17 but also another communication link 1604 with another vehicle. This allows for a group chat between operators of the vehicles 1600. Operators can talk, listen to other conversations, and/or not talk and only listen to multiple other drivers at the same time.

Figure 18:
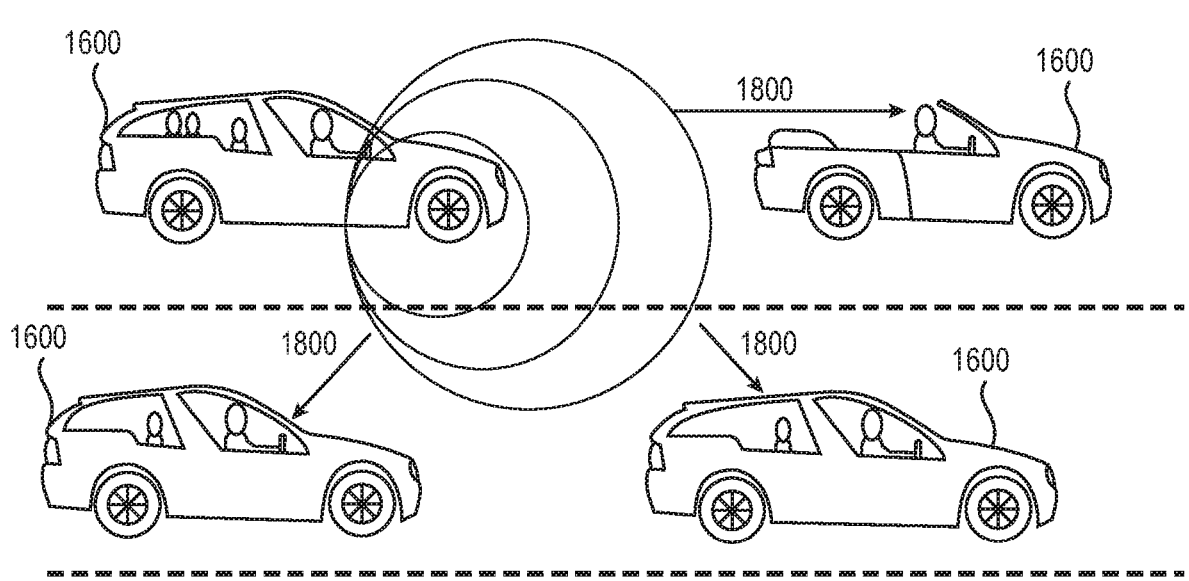
FIG. 18 shows a vehicle 1600 broadcasting to other vehicles 1600. A driver of a vehicle 1600 can broadcast/talk over a channel 1800 to multiple other vehicles 1600 at the same time within allowed range.

FIG. 18 shows a vehicle 1600 broadcasting to a plurality of other vehicles 1600 which are each equipped with a communication device 1400. An operator of a vehicle 1600 can broadcast/talk over a channel 1800 to a plurality of other vehicles 1600 at the same time within an allowed (or predetermined) range.

Figure 19:
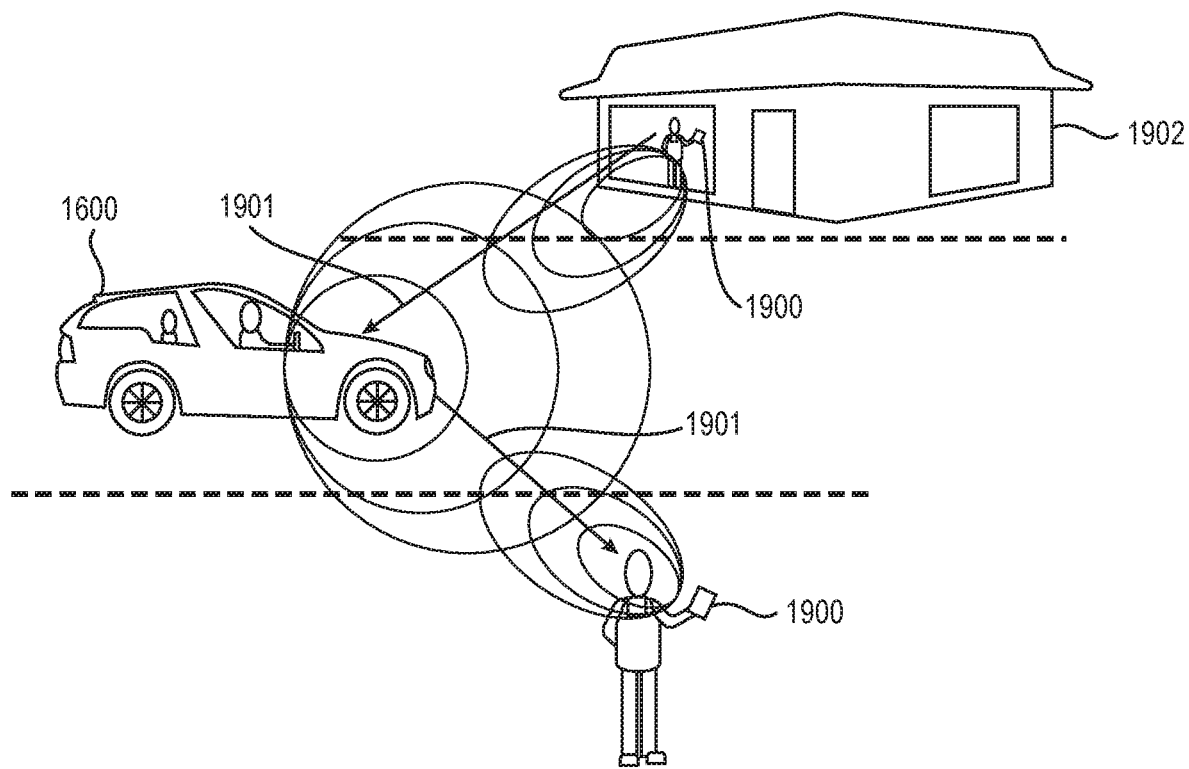
FIG. 19 shows a vehicle 1600 communicating through links 1901 with a plurality of wireless devices 1900 associated with individuals.

FIG. 19 shows a vehicle 1600 having a wireless communication device 1400 communicating through links 1901 with a plurality of wireless communication devices 1900 associated with individuals. (Wireless communication devices 1900 may be the same as wireless communication devices 1400 as described in this disclosure or may be smartphones, tablets or the like that are equipped with the application 1413). Operator of vehicle 1600 can talk to wireless devices 1900 located both on the street and inside a building 1902 (e.g., ordering food at McDonalds).

Figure 20:
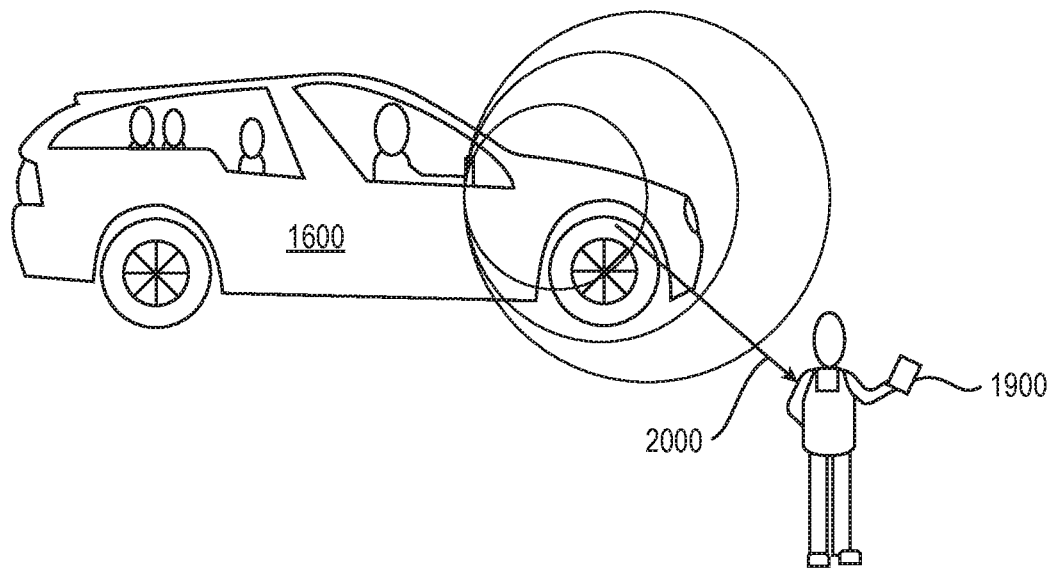
FIG. 20 shows a vehicle 1600 communicating with an individual having a wireless device 1900 through link 2000.

FIG. 20 shows a vehicle 1600 having a wireless communication device 1400 communicating with an person having a wireless communication device 1900 through link 2000. The instantaneous communication network 1500 allows for the operator of the vehicle 1600 to be able to see the person and their device 1900 and instantaneously act and talk to them peer to peer without any meaningful delay (just like an intercom).

Figure 21:
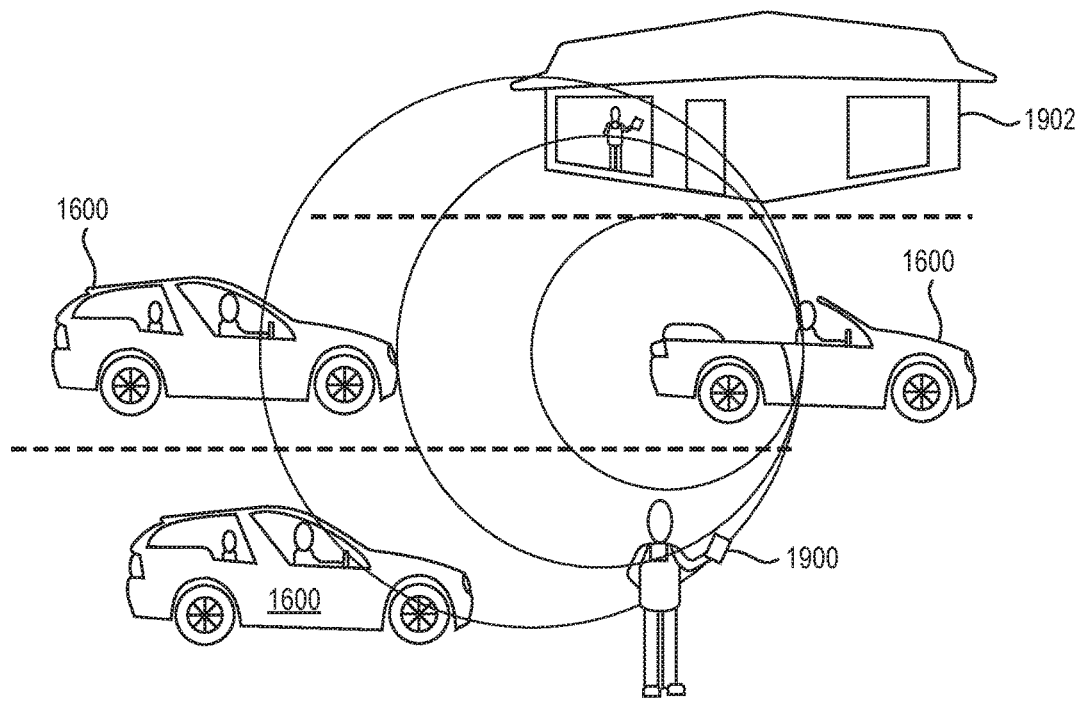
FIG. 21 shows a business in building 1902 advertising instantaneous specials to vehicles 1600 and with user associated wireless devices 1900.

FIG. 21 shows a business in building 1902 advertising instantaneous specials to vehicles 1600 with wireless communication devices 1400 and with user associated wireless devices 1900. The drivers of the vehicles 1600 and users associated with devices 1900 can interact with the advertising. Advertising can be changed instantaneously for on demand offers. Billboards located, for example, on the side of building 1902 can have an instantaneous network 1500 (or intercom system) built in to broadcast to vehicles 1600 and devices 1900.

Figure 22:
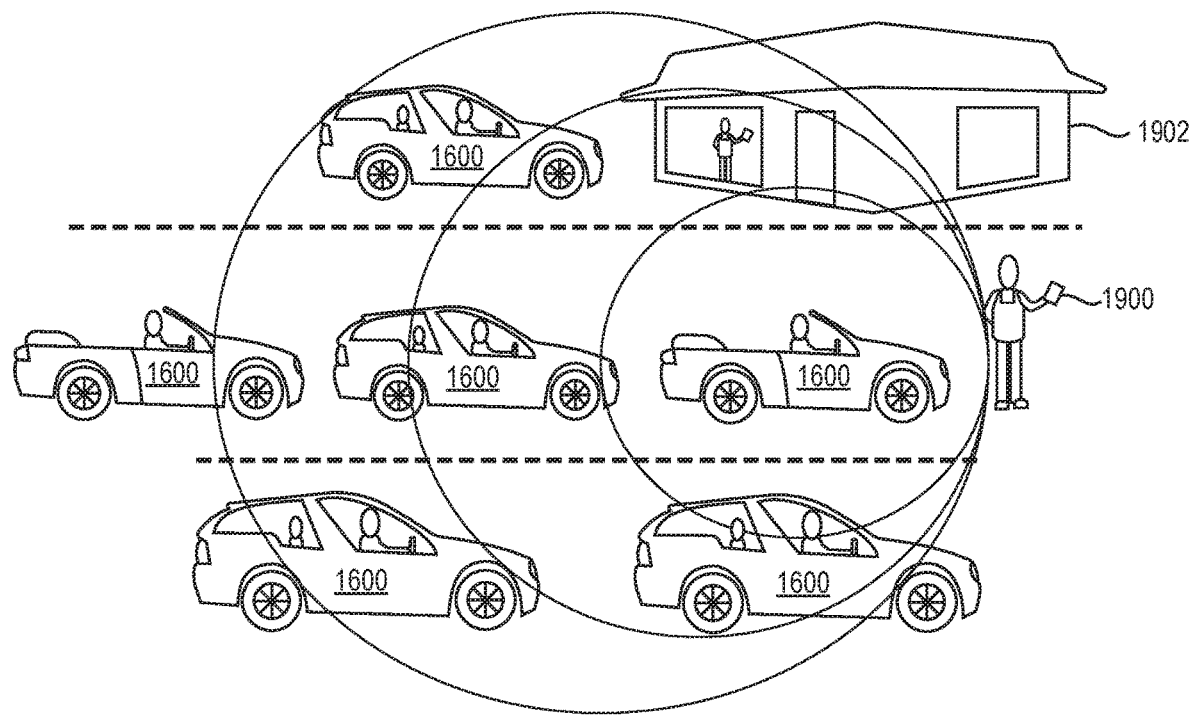
FIG. 22 shows business advertising instantaneous specials to vehicles 1600 and user associated wireless devices 1900.

FIG. 22 shows business advertising instantaneous specials to vehicles 1600 equipped with wireless communication devices 1400 and user associated wireless devices 1900. Vehicles 1600 and devices 1900 can interact with the advertising. Advertising can be changed instantaneously and on demand. Billboards located for example on buildings 1902 can have Instantaneous network 1500 systems built in. Businesses may, for example, broadcast that tor the next 20 minutes buy 1 get one free for all people in the parking lot.

Figure 23:
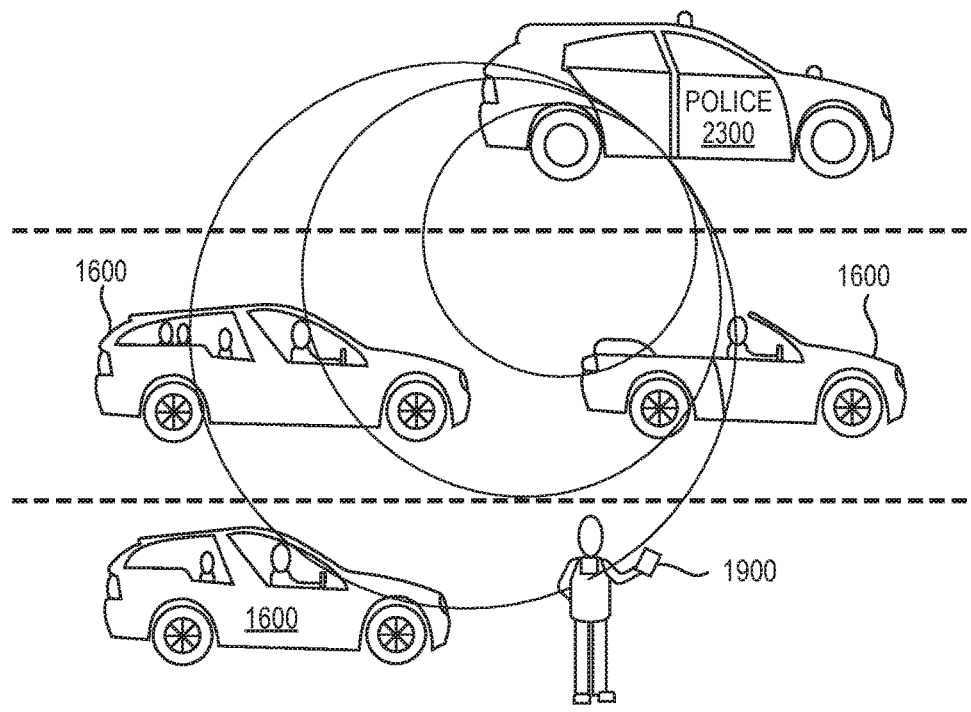
FIG. 23 shows an emergency system operating from an emergency vehicle 2300 for alerting vehicles 1600 and user operated wireless devices 1900 to danger in a specific area (e.g., safety Amber alert).

FIG. 23 shows an emergency instantaneous network system 1500 operating from a wireless communication device 1400 in an emergency vehicle 2300 for alerting vehicles 1600 with wireless communication devices 1400 and user operated wireless devices 1900 to danger in a specific area (e.g., safety Amber alert).

Figure 24:
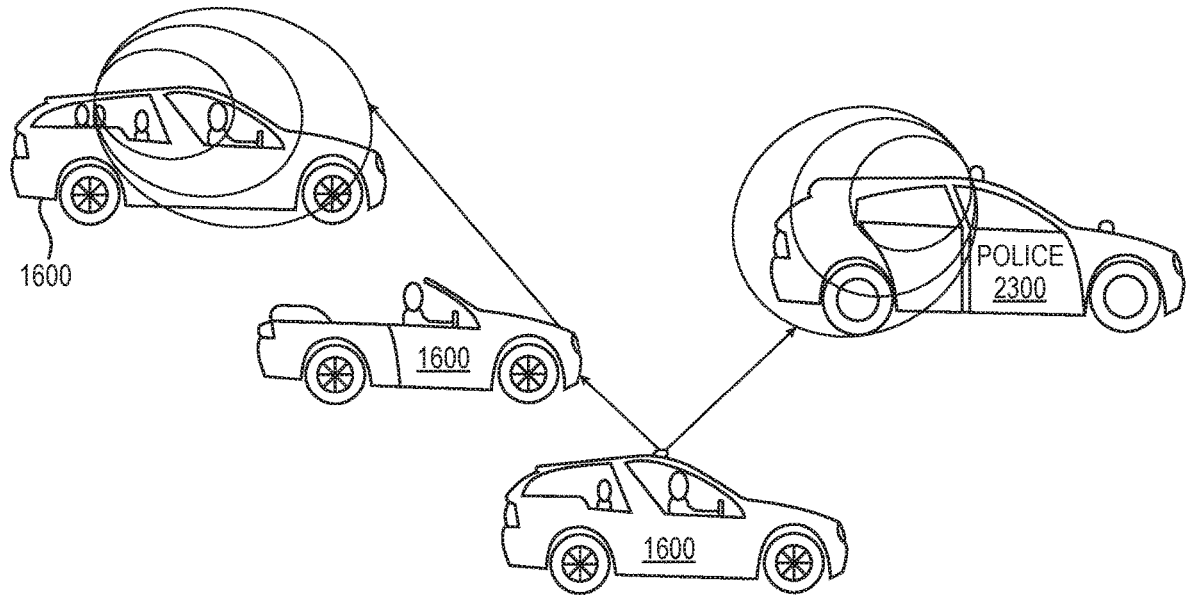
FIG. 24 shows another emergency system from an emergency vehicle 2300 for alerting vehicles 1600 and user operated wireless devices 1900 to danger in a specific area.

FIG. 24 shows another emergency instantaneous network system 1500 from an emergency vehicle 2300 equipped with a wireless communication device 1400 for alerting vehicles 1600 with wireless communication devices 1400 and user operated wireless devices 1900 to danger in a specific area. An instantaneous network system 1500 allows for a longer range communication using a bypass mode. Using the radios in a plurality of vehicles 1600 to create a mesh network.

FIGS. 25A-25C show the steps in setting up a chat on the instantaneous network 1500. In step 1 of FIG. 25A the instantaneous network (or intercom) application 1413 is opened on display 1412 and it is seen who is willing to chat. In step 2 in FIG. 25B, the operator of the communication device 1400 chooses the located person by clicking on their icon 1440. In step 3 shown in FIG. 25C, the operator may start chatting and when finished, click on the icon 1440 to end the communication.

FIGS. 26A-26C show the steps in setting up a broadcast. In step 1 shown in FIG. 26A the instantaneous network system 1500 (or intercom) application 1413 is opened up and the operator checks to see who is willing to listen. In step 2 shown in FIG. 26B, icons 1440 are chosen. In step 3 shown in FIG. 26C the broadcast is started and end broadcasting is entered by the operator to conclude the broadcast.

FIGS. 27A-27C show the steps in sending an emoji 1441. In step 1 shown in FIG. 27A, the operator opens the instantaneous network system (or intercom) application 1413. In step 2 shown in FIG. 27B, the operator chooses an icon 1440 representing a person, the icon is held down and an emoji 1441 chosen to be sent. FIG. 27C shows the emoji 1441 being sent (which may be rejected).

FIGS. 28A-28C show the steps in advertising from a store. In step 1 shown in FIG. 28A the instantaneous network system (or intercom) application 1413 is opened on display 1412. In step 2 shown in FIG. 28B the icons 1440 and/or emojis 1441 are chosen by the operator. In step 28C, discounts/coupons are sent to the vehicles 1600. For example, for the next 20 minutes buy one and get one free for all the vehicles 1600 in the parking lot.

FIG. 29 shows the instantaneous network system application 1413 using a voice. The instantaneous network (or intercom) application 1413 is opened and a person with a wireless communication device 1400 is selected on the display 1412. Each person/icon 1440 is labeled (e.g., 1, 2, John). Only icons 1440 within the communication range will have labels/names. The icons 1440 can be selected by voice and emojis 1441 can be sent by voice.

Figure 30:
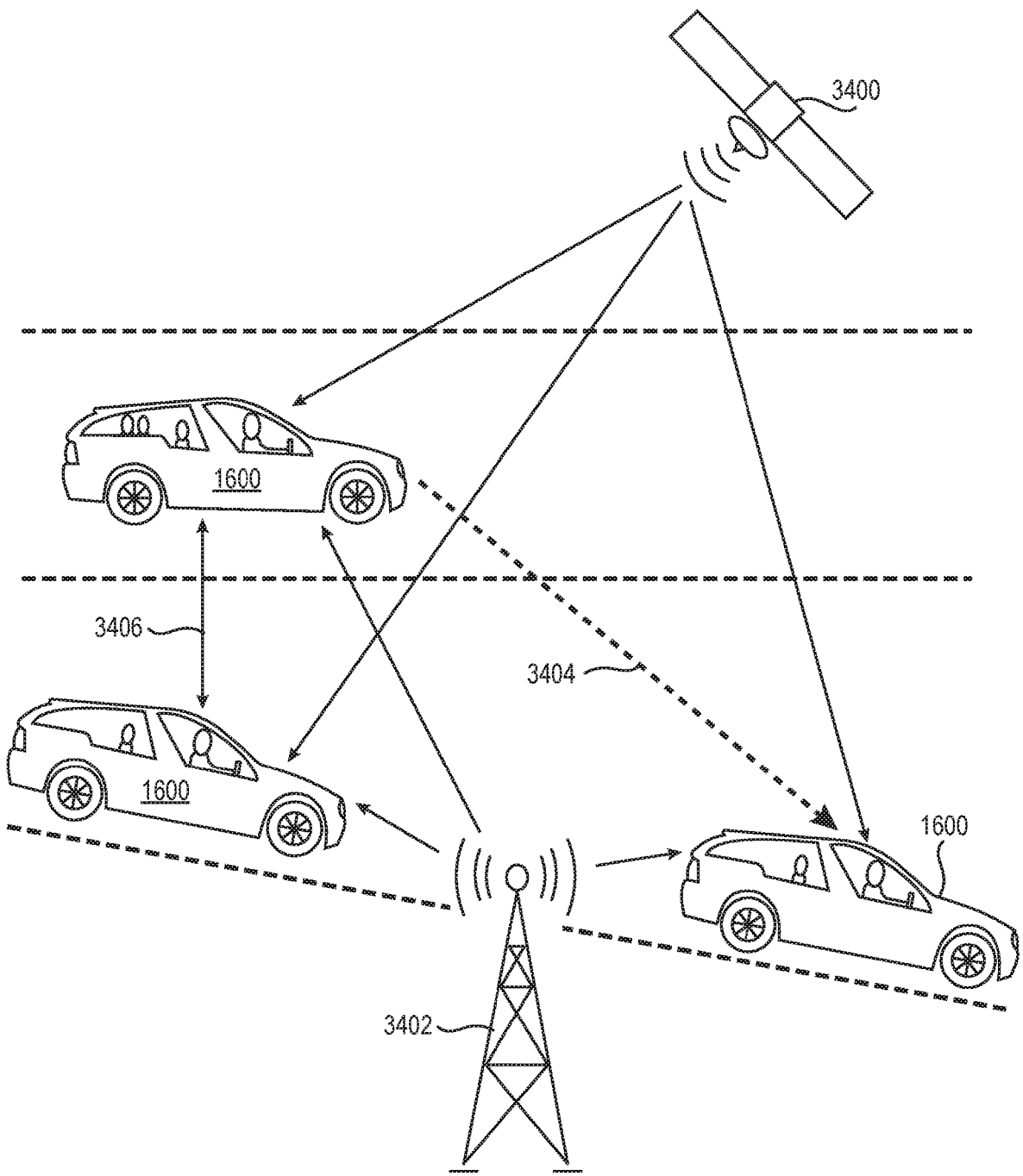
FIG. 30 shows that the information generated by GPS from a satellite 3400, radar, cellular network 3402, and other RF equipment may be used determine the location of other vehicles.

FIG. 30 shows that the information generated by a global positioning system (GPS) from a satellite 3400, radar, cellular network 3402, and other RF equipment may be used to determine the location of other vehicles 1600 by the wireless communication device 1400. Based on the location of the vehicles 1600, the instantaneous network system 1500 (or intercom) decides if the second vehicle 1600 is in the range of direct, peer to peer communication. Reference 3404 indicates the second vehicle 1600 is too far and reference 3406 indicates the second vehicle 1600 is within range.

Figure 31:
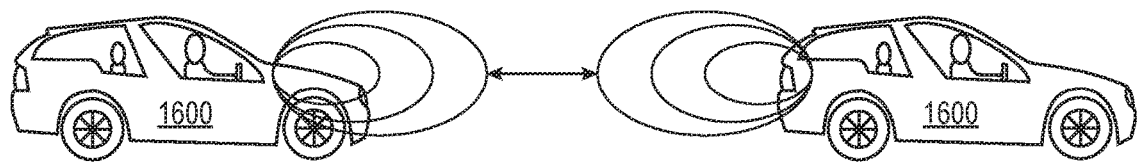
FIG. 31 shows a secure short range, direct peer to peer communication (similar to an intercom system) which can be achieve via WiFi Peer to Peer, Bluetooth, or any other communication standard on in a range of communication frequencies (e.g., 20 MHz-100 GHz).

FIG. 31 shows a secure short range, direct peer to peer communication (similar to an intercom system) which can be achieve via WiFi Peer to Peer, Bluetooth, or any other communication standard on in a range of communication frequencies (e.g., 20 MHz-100 GHz).

Figure 32:
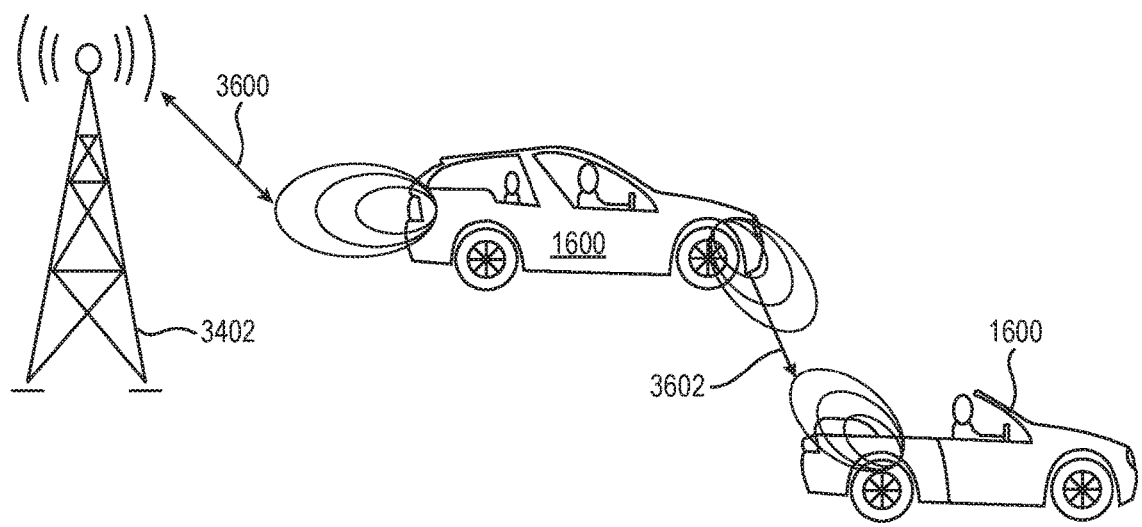
FIG. 32 shows live streaming with secure short range peer to peer communication, similar to an intercom system, can be achieve via WiFi Peer to Peer, Bluetooth, or any other communication standard on any communication frequency (e.g. 20 MHz-100 GHz).

FIG. 32 shows live streaming with secure short range, direct peer to peer communication (similar to an intercom system), which can be achieve via WiFi Peer to Peer, Bluetooth, or any other communication standard on in a range of communication frequencies (e.g., 20 MHz-100 GHz). Communication link 3600 is a long range communication link such as 3G, 4G and 5G and communication link 3602 is a short range, direct communication such as WiFi, Bluetooth, two way radio, very high frequency (VHF), and ultra high frequency (UHF).

Figure 33:
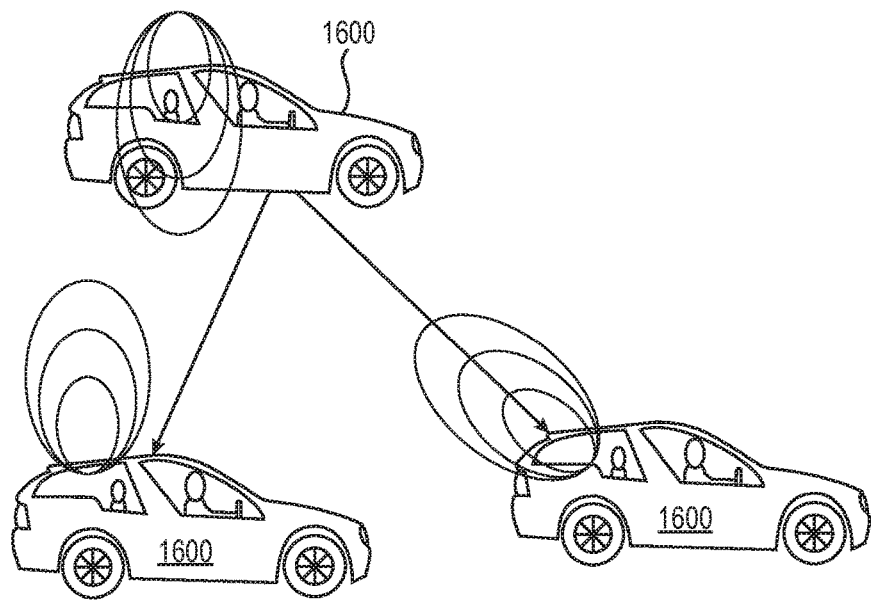
FIG. 33 shows a 5G mmWave example.

FIG. 33 shows a 5G mmWave embodiment. Short range communication using millimeter wave communications (such as 5G on frequencies 28 GHz, 60 GHz, 38 GHz, or 100 GHz) to transmit large amounts of data very quickly. Due to their high bandwidth, mmWave is great for large data and speed, but not for distance, making it ideal for short range communications. In an exemplary embodiment, children inside a vehicle 1600, watching other children in other vehicles 1600 on the display screen 1412 of the wireless communication device 1400, may set up an instantaneous network 1500 to exchange videos, communications or the like.

Figure 34:
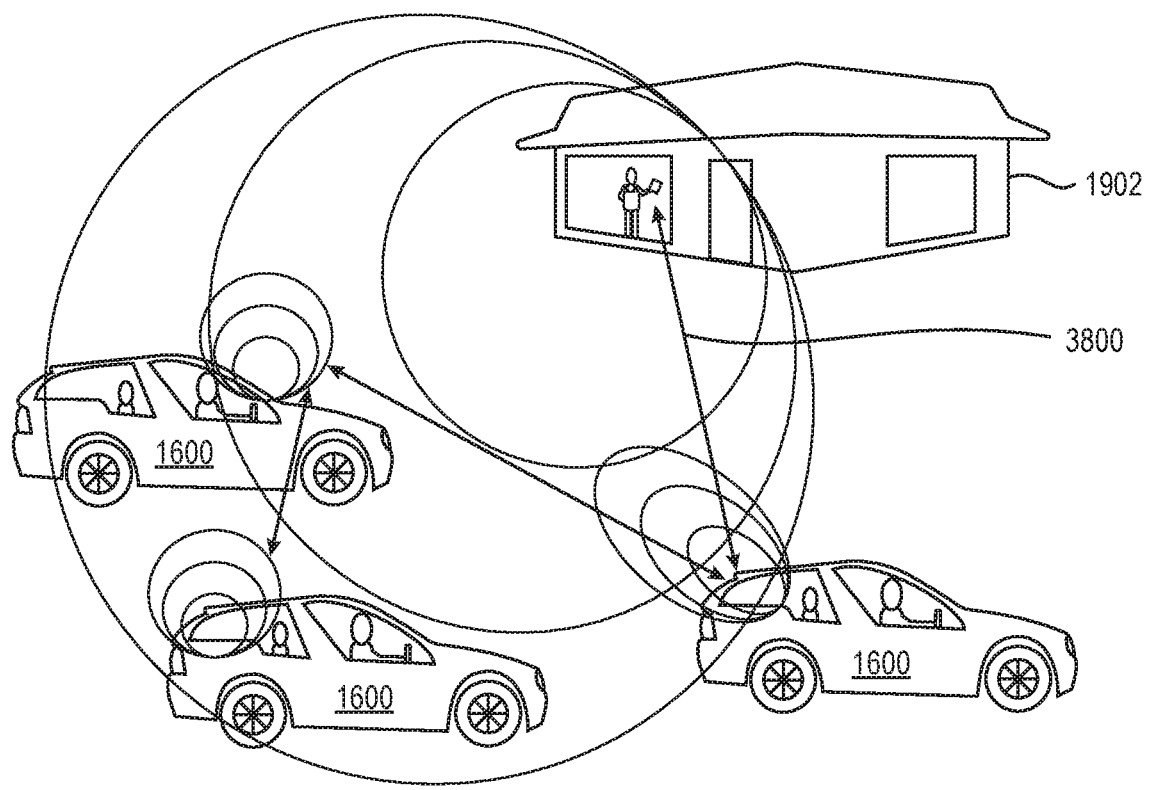
FIG. 34 illustrates a large amount of data over a 5G mmWave link 3800 being exchanged using an instantaneous network system 1500 (or intercom system).

FIG. 34 illustrates a large amount of data over a 5G mmWave link 3800 being exchanged using the instantaneous network system 1500 (or intercom system). For example, it may be advertising to vehicles 1600 equipped with wireless communication devices 1400 through link 3800 for the next 20 minutes to offer buy two, get one free.

Figure 35:
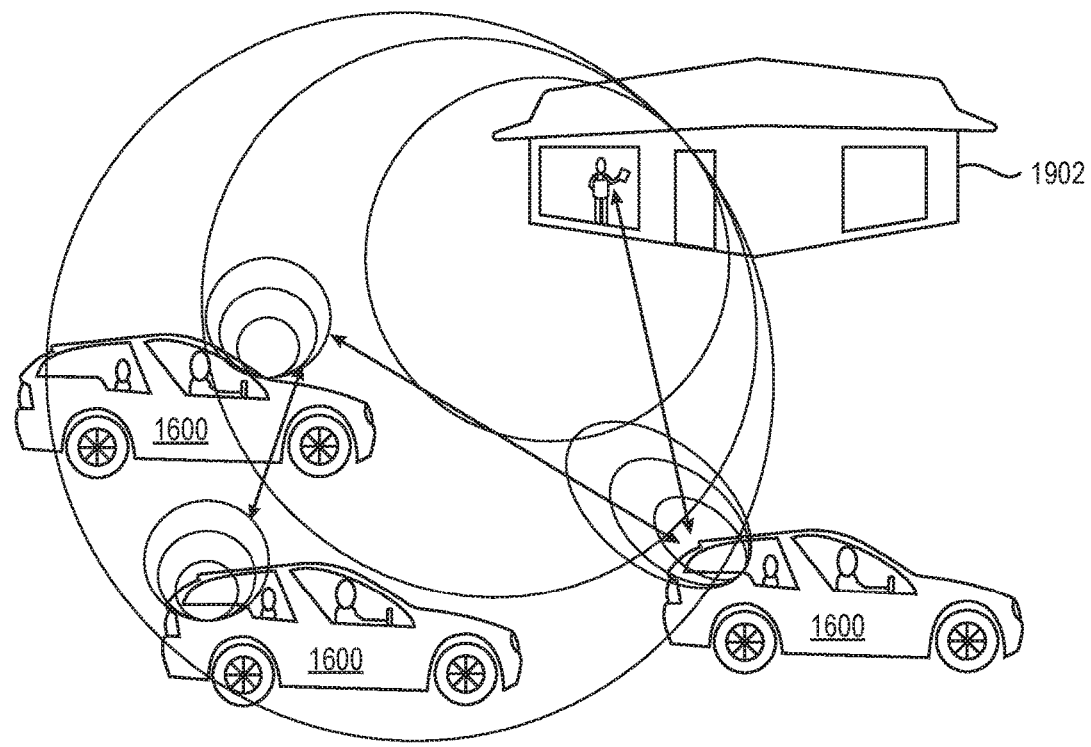
FIG. 35 shows a large amount of data being exchanged using an instantaneous network system 1500 (or intercom system).

FIG. 35 shows a large amount of data being exchanged using the instantaneous network system 1500 (or intercom system) between the wireless communication device 1400 in building 1902 and the wireless communication devices 1400 in vehicles 1600.

Figure 36:
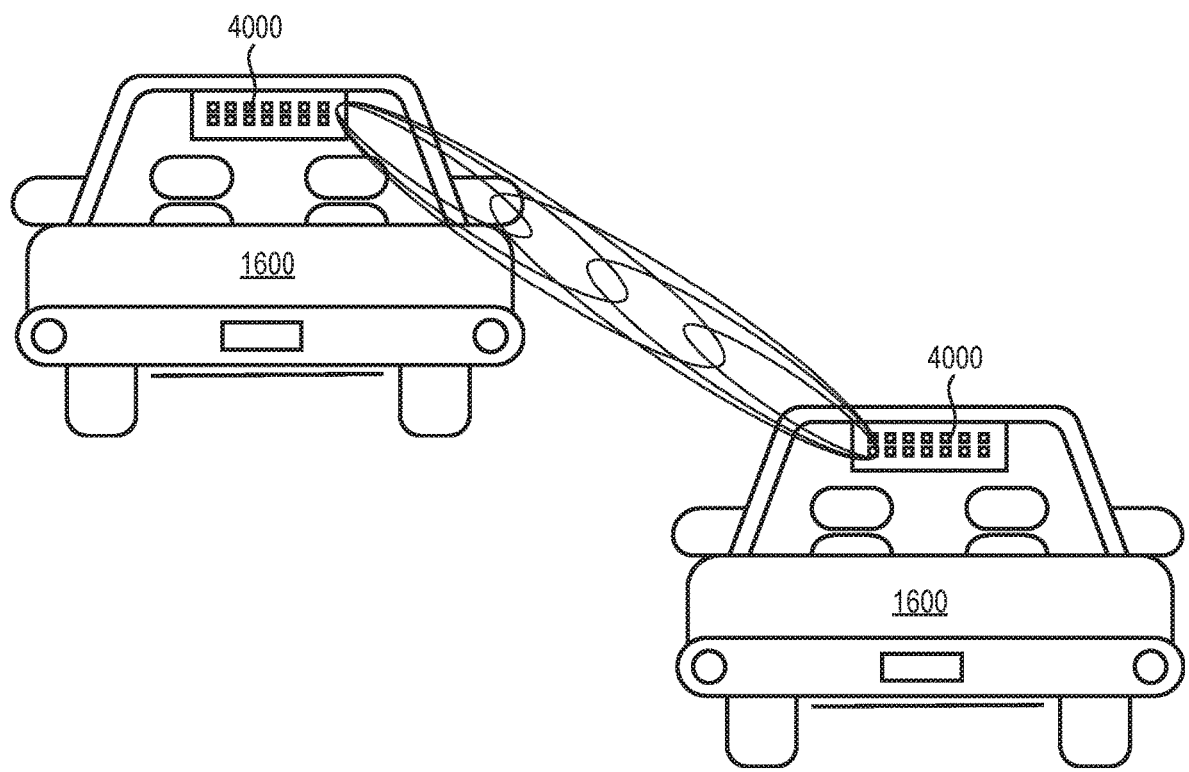
FIG. 36 shows short range communication using millimeter wave communications (such as 5G on 28 Hz, 60 GHz, 38 GHz, 100 GHz) to transmit large amounts of data quickly.

FIG. 36 shows short range communication instantaneous network 1500 using millimeter wave communications (such as 5G on frequencies such as 28 Hz, 60 GHz, 38 GHz, or 100 GHz) to transmit large amounts of data quickly. Due to their high bandwidth, mmWave is great for large data and speed, but not for distance, making it ideal for short range communications. A low cost antenna array 4000 made be made and/or printed onto a film material built into the car windows or attached anywhere (including on top) of the vehicle 1600. Makes beam forming and steering possible, traditional approach such as horn antenna would not have such features. The antenna 4000 can be baked into the glass window at low cost. In one embodiment, antenna 4000 may be connected to the wireless communication device 1400. Or in an alternative embodiment, antenna 4000 may take the place of antenna 1428 (discussed above) of the wireless communication device 1400.

Figure 37:
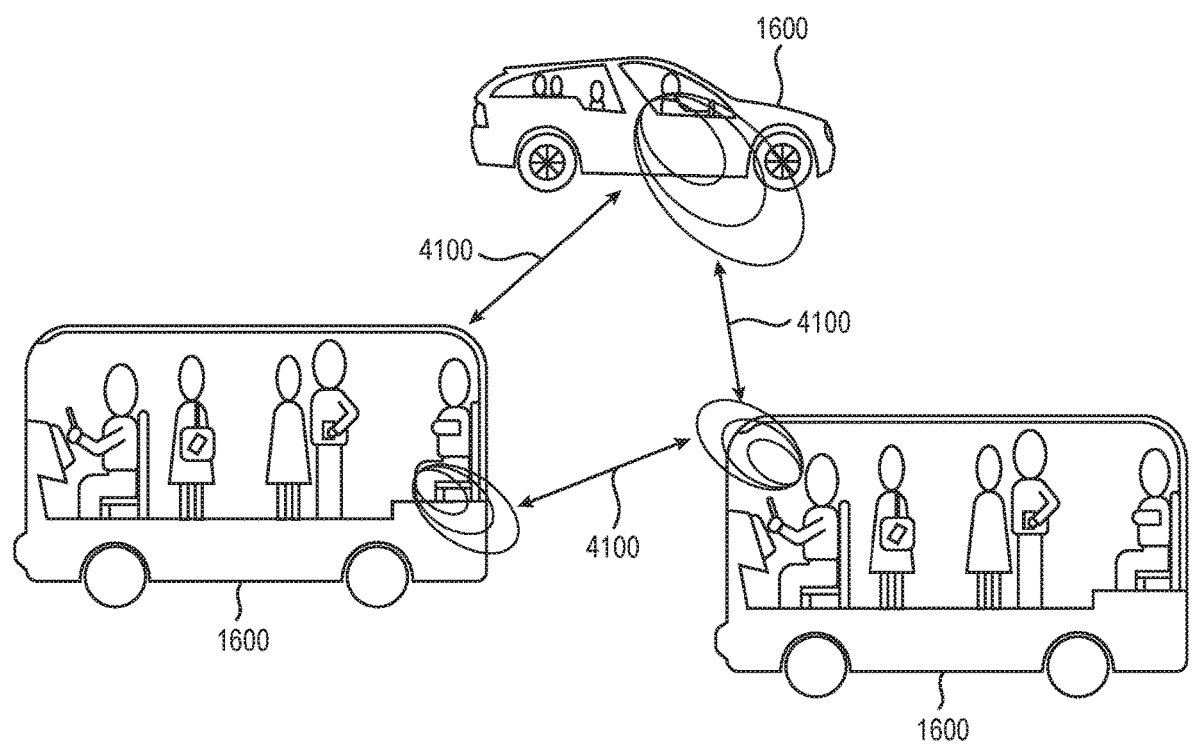
FIG. 37 is another 5G mmWave instantaneous network 1500 embodiment with a large amount of data being exchanged between vehicles 1600 having wireless communication devices 1400 using links 4100.

FIG. 37 is another 5G mmWave instantaneous network 1500 embodiment with a large amount of data being exchanged between vehicles 1600 having wireless communication devices 1400 using links 4100.

Figure 38:
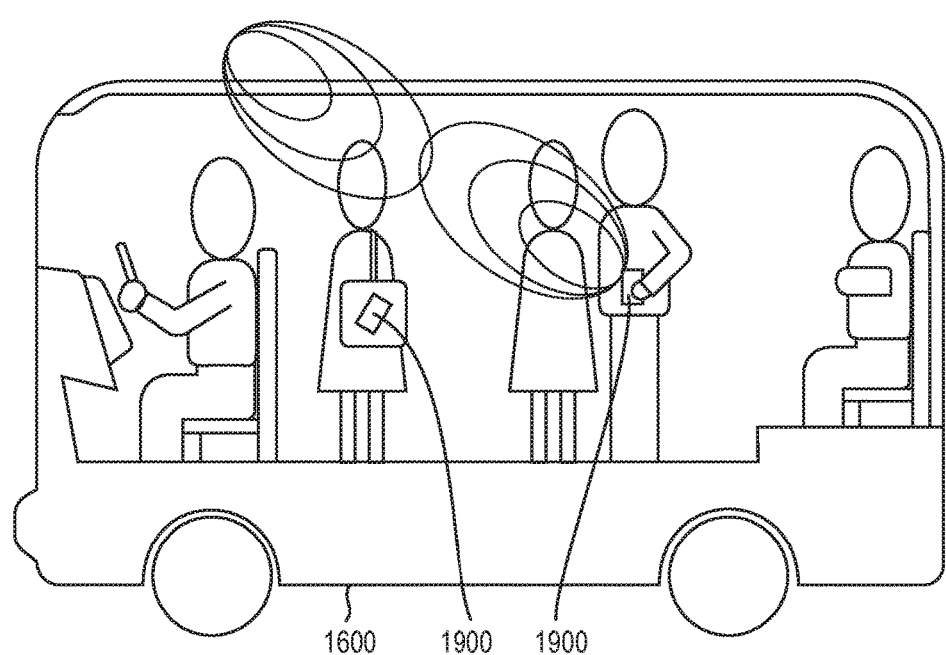
FIG. 38 is another 5G mmWave instantaneous network 1500 embodiment with a large amount of data being exchanged between operators with wireless devices 1900 inside a vehicle 1600 (e.g., bus).

FIG. 38 is another 5G mmWave instantaneous network 1500 embodiment with a large amount of data being exchanged between operators with wireless devices 1900 inside a vehicle 1600 (e.g., bus).

Figure 39:
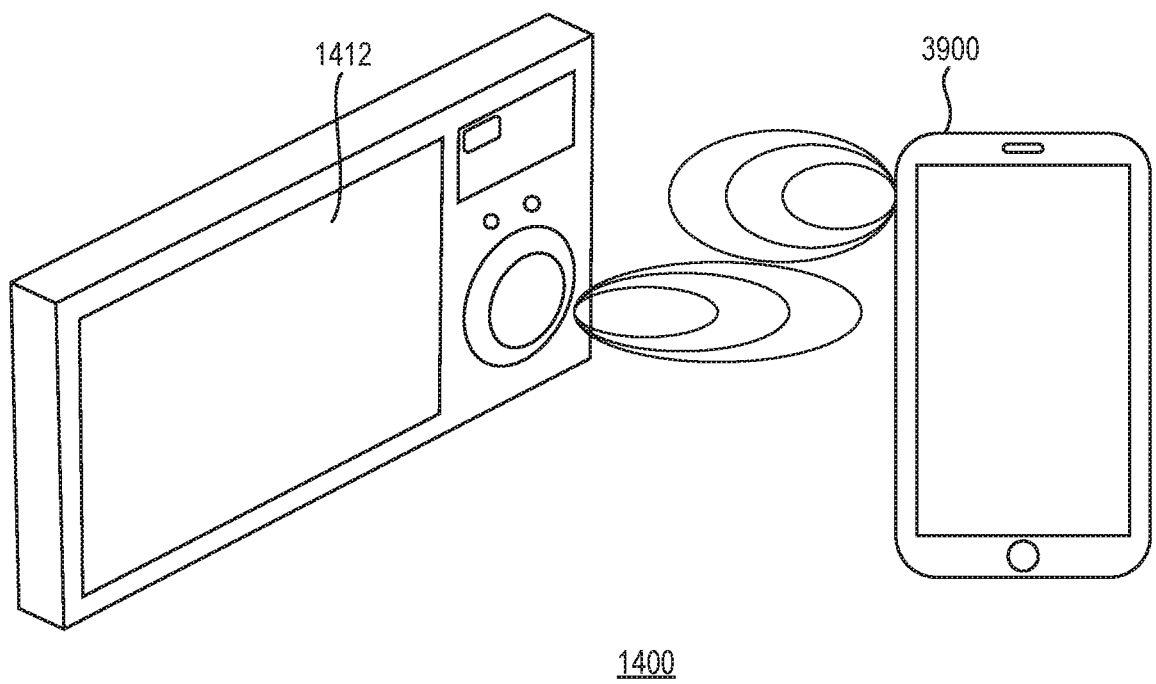
FIG. 39 illustrates that the communication device 1400 can be programmed and accessed via a phone 3900 or personal computer (e.g., WiFi, Bluetooth, or Zigbee) to adjust desired settings.

FIG. 39 illustrates that the communication device 1400 can be programmed and accessed via a phone 3900 or personal computer (e.g., WiFi, Bluetooth, or Zigbee) to adjust desired settings.

Figure 40A:
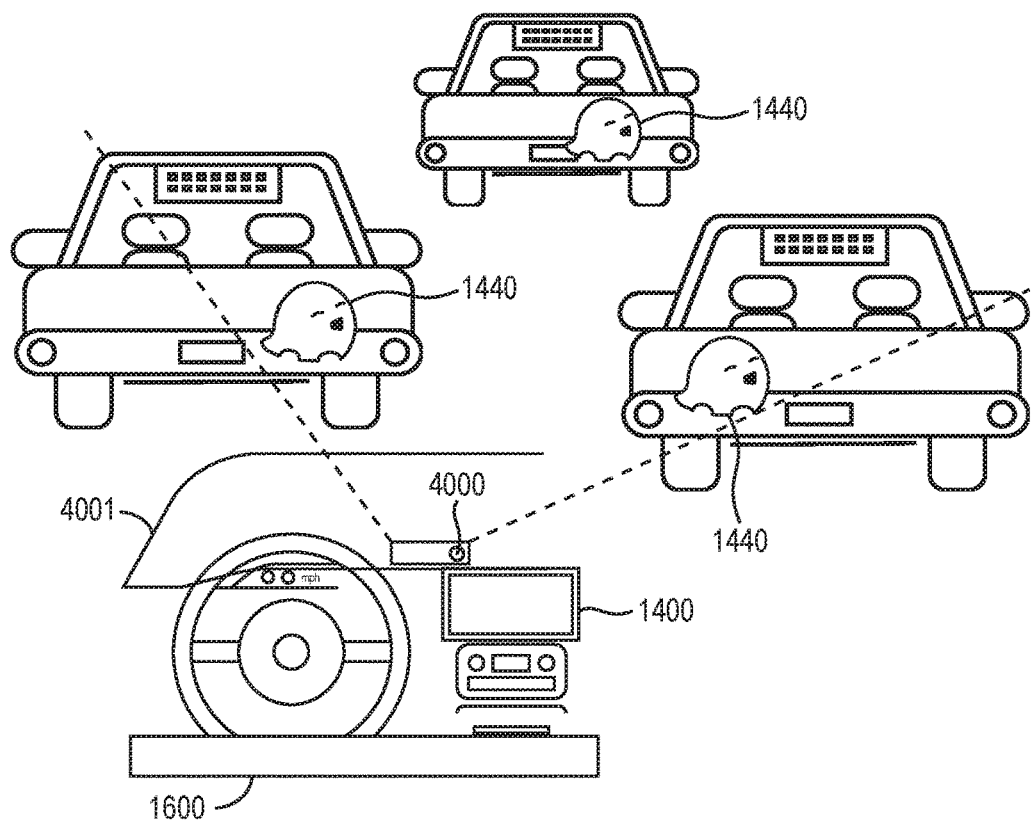
FIGS. 40A-40C show the communication device 1400 with augmented reality (AR).
Figure 40B:
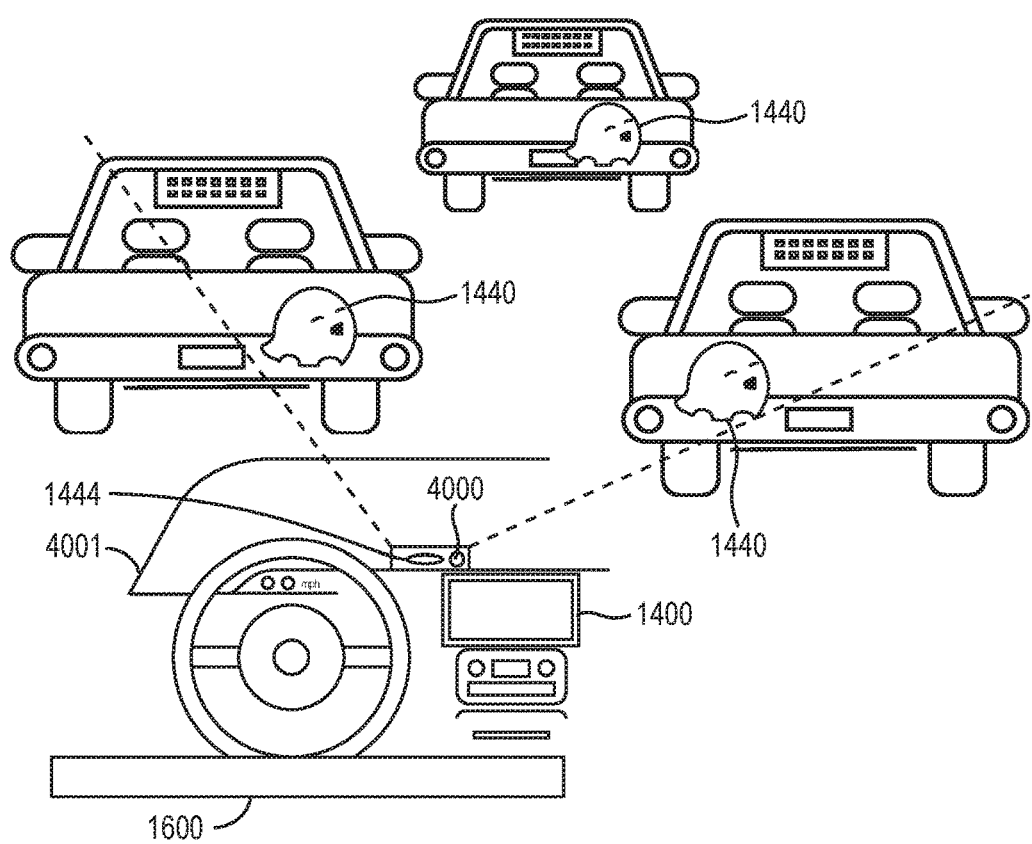
Figure 40C:
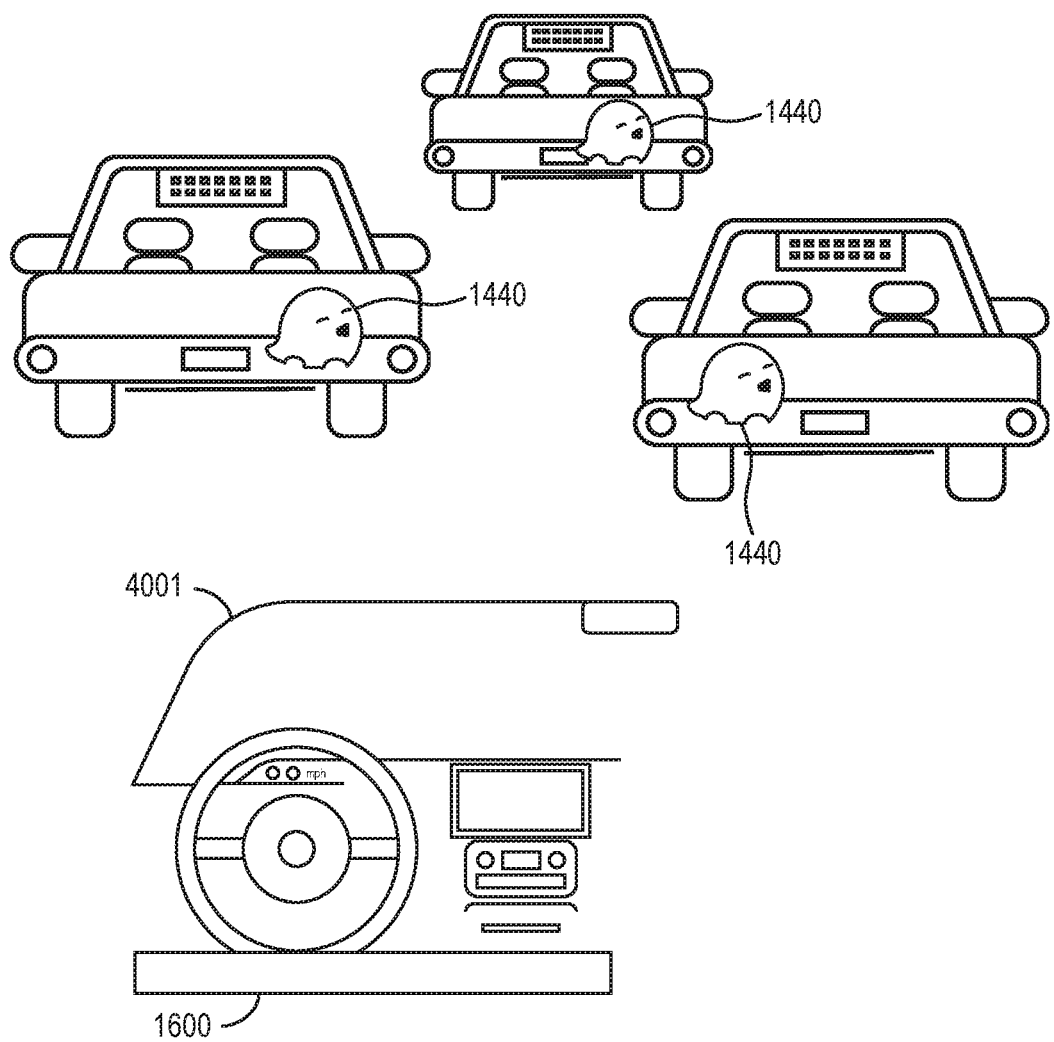

FIGS. 40A-40C show the communication device 1400 with augmented reality (AR). FIG. 40A shows the communication device 1400 with AR built into a Heads-Up Display (HUD) 4000. In alternate embodiments, the communication device 1400 and HUD 400 can be combined into the same wireless communication device 1400. The screen of the display 1412 is projected by the HUD 4000 onto the windshield 4001 of the vehicle 1600. An overlay 4002 is created on the windshield to show proximate icons (and avatars) 1440 and emojis 1441. The icons 1440 may be selected by hand gestures. The hand gestures may be detected by mmWaves to detect hand motions and/or voice controls. The icons 1440 may be projected in different colors so the voice control can be directed toward the color of the icon 1440 to be selected. FIG. 40B shows the communication device 1400 with HUD 4000 having a built in eye tracking 4004. Icons 1440 can be selected by looking at a particular icon with the eye tracking technology. FIG. 40C shows communication device 1400 with AR built into the windshield 4001. The windshield 4001 is either wired or wirelessly connected to the communication device 1400 so that the icons 1440 and emojis 1441 may be displayed.

Approximately: refers herein to a value that is almost correct or exact. For example, "approximately" may refer to a value that is within 1 to 10 percent of the exact (or desired) value. It should be noted, however, that the actual threshold value (or tolerance) may be application dependent. For example, in some embodiments, "approximately" may mean within 0.1% of some specified or desired value, while in various other embodiments, the threshold may be, for example, 2%, 3%, 5%, and so forth, as desired or as required by the particular application.

Automatically: refers herein to an action or operation performed by a computer system (e.g., software executed by the computer system) or device (e.g., circuitry, programmable hardware elements, ASICs, etc.), without user input directly specifying or performing the action or operation. Thus the term "automatically" is in contrast to an operation being manually performed or specified by the user, where the user provides input to directly perform the operation. An automatic procedure may be initiated by input provided by the user, but the subsequent actions that are performed "automatically" are not specified by the user, i.e., are not performed "manually", where the user specifies each action to perform. For example, a user filling out an electronic form by selecting each field and providing input specifying information (e.g., by typing information, selecting check boxes, radio selections, etc.) is filling out the form manually, even though the computer system must update the form in response to the user actions. The form may be automatically filled out by the computer system where the computer system (e.g., software executing on the computer system) analyzes the fields of the form and fills in the form without any user input specifying the answers to the fields. As indicated above, the user may invoke the automatic filling of the form, but is not involved in the actual filling of the form (e.g., the user is not manually specifying answers to fields but rather they are being automatically completed). The present specification provides various examples of operations being automatically performed in response to actions the user has taken.

Communication: in this disclosure, devices that are described as in "communication" with each other or "coupled" to each other need not be in continuous communication with each other or in direct physical contact, unless expressly specified otherwise. On the contrary, such devices need only transmit to each other as necessary or desirable, and may actually refrain from exchanging data most of the time. For example, a machine in communication with or coupled with another machine via the Internet may not transmit data to the other machine for long period of time (e.g. weeks at a time). In addition, devices that are in communication with or coupled with each other may communicate directly or indirectly through one or more intermediaries.

Configured To: various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits. Various components may be described as performing a task or tasks, for convenience in the description. Such descriptions should be interpreted as including the phrase "configured to." Reciting a component that is configured to perform one or more tasks is expressly intended not to invoke 35 U.S.C. § 112(f) interpretation for that component.

Although process (or method) steps may be described or claimed in a particular sequential order, such processes may be configured to work in different orders. In other words, any sequence or order of steps that may be explicitly described or claimed does not necessarily indicate a requirement that the steps be performed in that order unless specifically indicated. Further, some steps may be performed simultaneously despite being described or implied as occurring non-simultaneously (e.g., because one step is described after the other step) unless specifically indicated. Moreover, the illustration of a process by its depiction in a drawing does not imply that the illustrated process is exclusive of other variations and modifications thereto, does not imply that the illustrated process or any of its steps are necessary to the embodiment(s), and does not imply that the illustrated process is preferred.

Means Plus Function Language: to aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

Ranges—it should be noted that the recitation of ranges of values in this disclosure are merely intended to serve as a shorthand method of referring individually to each separate value falling within the range, unless otherwise indicated herein, and each separate value is incorporated into the specification as if it were individually recited herein. Therefore, any given numerical range shall include whole and fractions of numbers within the range. For example, the range "1 to 10" shall be interpreted to specifically include whole numbers between 1 and 10 (e.g., 1, 2, 3, . . . 9) and non-whole numbers (e.g., 1.1, 1.2, . . . 1.9).

The foregoing description and embodiments have been presented for purposes of illustration and description and are not intended to be exhaustive or to limit the embodiments in any sense to the precise form disclosed. Also, many modifications and variations are possible in light of the above teaching. The embodiments were chosen and described to best explain the principles of the disclosure and its practical application to thereby enable others skilled in the art to best use the various embodiments disclosed herein and with various modifications suited to the particular use contemplated. The actual scope of the invention is to be defined by the claims.

The invention claimed is:

1. A system comprising:
   a first wireless communication device located in a vehicle and capable of sending and receiving radio frequency wave signals having a microphone, a speaker to enable communications, and a touch display screen displaying avatars which represent operators of a plurality of wireless communication devices in proximity to the first wireless communication device;

an antenna array attached to the vehicle and the first wireless communicative device and capable of forming and steering the radio frequency wave signals; and wherein the first wireless communication device is capable of receiving a selection of the avatar of at least one of the operators to create and withdraw a direct, anonymous, peer-to-peer communication link with the operator of a second wireless communication device to form an instantaneous social network.

2. The system of claim 1, wherein the second wireless communication device is capable of being randomly selected by the first wireless communication device from a plurality of wireless communication devices which are in proximate location to the first wireless device.

3. The system of claim 1, wherein the second wireless communication device is capable of being selected through machine learning by the first wireless communication device from a plurality of proximate wireless communication devices.

4. The system of claim 1, the first wireless communication device capable of being programmed using at least one from a group consisting of a smartphone, a tablet, and a personal computer through a wireless connection via at least one from a group consisting of Bluetooth, WiFi, and ZigBee.

5. The system of claim 1, wherein the radio frequency signals are in the millimeter wave range.

6. The system of claim 1, wherein the first wireless communication device further comprises a battery for power.

7. The system of claim 1, the first wireless communication device has a heads up display to show the plurality of wireless communication devices which are proximate to the first communication device as avatars.

8. The system of claim 1, the first wireless communication device has augmented reality on the display screen to provide details about the plurality of wireless communication devices which are proximate to the first communication device.

9. The system of claim 1, wherein the first wireless communication device has an RF identification (RFID) chip to signal identification information to the plurality of wireless communication devices.

10. The system of claim 1, wherein the first wireless communication device is capable of using eye tracking technology to monitor an operator and be controlled by the operator.

11. The system of claim 10, wherein the first wireless communication device can receive physical gesture inputs of the operator to control communications with the second wireless communication device.

12. The system of claim 1, wherein the first wireless communication device is capable of being controlled via an operator's voice.

13. The system of claim 1, wherein the first wireless communication device operates in a frequency range of 400 MHz to 100 GHz.

14. The system of claim 1, wherein the first wireless communication device is capable of projecting a visual display on a windshield of a vehicle.

15. The system of claim 1, wherein the first wireless communication device is capable of operating using at least one operating system of the group consisting of Android Platform, Windows, iOS, and WebOS.

16. The system of claim 1, wherein the first wireless communication device is configured to connect to a plurality of proximate wireless communication devices at the same time.

17. The system of claim 1, wherein the first wireless communication device can broadcast to a plurality of proximate wireless communication devices at the same time.

18. The system of claim 1, wherein the first wireless communication device can operate in communication with the second wireless communication device without fixed base station infrastructure.

19. A system for forming an instantaneous social network comprising:

a first wireless communication device located in a vehicle and capable of sending and receiving radio frequency wave signals having a microphone, a speaker to enable communications, and a touch display screen displaying avatars which represent operators of a plurality of wireless communication devices in proximity to the first wireless communication device;

an antenna array attached to the vehicle and the first wireless communicative device and capable of forming and steering the radio frequency wave signals;

wherein the first wireless communication device is capable of receiving broadcasts from a plurality of proximity wireless communication devices including a second wireless communication device; and at least one of the plurality of avatars on the first wireless communication device which is capable of being activated to transmit wireless signals directly to and receive signals from the second wireless communication device to form a direct, anonymous communication link.

20. The system of claim 19, wherein the first wireless communication device uses at least one wireless standard from the group consisting of long term evolution, (LTE), internet of things (IOT), 5G new radio (NR), non-standalone (NSA) 5G, standalone (SA) 5G, Bluetooth, and WiFi to communicate with the second wireless communication device.

21. The system of claim 19, wherein the first wireless communication device can operate in a frequency range of 400 MHz to 100 GHz.

22. A system for forming an instantaneous social network comprising:

a first wireless communication device located in a vehicle and capable of sending and receiving radio frequency wave signals having a display screen and multi-mode and multi-frequency capabilities, an antenna array attached to the vehicle and the first wireless communicative device and capable of forming and steering the radio frequency wave signals;

wherein the first wireless communication device when activated is configured to:

send signals directly to and receive signals directly from a plurality of proximate wireless communication devices, wherein operators of said plurality of proximate wireless communication devices appear as a plurality of avatars on the display screen;

receive a selection of one of the plurality of avatars; and form a direct, anonymous, peer-to-peer communication link between the first wireless communication device and the selected proximate wireless communication device.

23. The system of claim 22, wherein the first wireless communication device uses at least one wireless standard from the group consisting of long term evolution, (LTE), internet of things (IOT), 5G new radio (NR), non-standalone (NSA) 5G, standalone (SA) 5G, Bluetooth, and WiFi to communicate with the second wireless communication device.

24. The system of claim 22, wherein the first wireless communication device operates in a frequency range of 400 MHz to 100 GHz.

\* \* \* \* \*